(12) United States Patent
Arad Hadar et al.

(10) Patent No.: US 12,708,388 B2
(45) Date of Patent: Aug. 18, 2026

(54) THROMBECTOMY SYSTEM AND METHODS OF EXTRACTING A THROMBUS FROM A THROMBUS SITE IN A BLOOD VESSEL OF A PATIENT

(71) Applicant: ANACONDA BIOMED, S.L., Barcelona (ES)

(72) Inventors: Ofir Arad Hadar, Sant Cugat del Vallès (ES); Iñaki Galve Murillo, Barcelona (ES)

(73) Assignee: ANACONDA BIOMED, S.L., Sant Quirze del Vallès (ES)

( * ) Notice: Subject to any disclaimer, the term of this patent is extended or adjusted under 35 U.S.C. 154(b) by 758 days.

(21) Appl. No.: 17/291,696

(22) PCT Filed: Nov. 12, 2019

(86) PCT No.: PCT/EP2019/080993
§ 371 (c)(1),
(2) Date: May 6, 2021

(87) PCT Pub. No.: WO2020/099386
PCT Pub. Date: May 22, 2020

(65) Prior Publication Data

US 2022/0000500 A1 Jan. 6, 2022

(30) Foreign Application Priority Data

Nov. 13, 2018 (EP) .................................... 18382800

(51) Int. Cl.
*A61B 17/221* (2006.01)
*A61B 17/22* (2006.01)
(Continued)

(52) U.S. Cl.
CPC .. *A61B 17/221* (2013.01); *A61B 2017/22034* (2013.01); *A61B 2017/22079* (2013.01);
(Continued)

(58) Field of Classification Search
CPC ........ A61B 17/221; A61B 2017/22034; A61B 2017/22079; A61B 2017/2212;
(Continued)

(56) References Cited

U.S. PATENT DOCUMENTS 4,574,176 A 3/1986 Sharp
4,794,231 A 12/1988 Banas et al.
(Continued)

FOREIGN PATENT DOCUMENTS

AU 2018274903 B2 4/2020
CN 102973332 A 3/2013
(Continued)

OTHER PUBLICATIONS

Arad et al.; U.S. Appl. No. 62/760,786 entitled "Thrombectomy system comprising an expandable tip aspiration catheter and clot-capture element," filed Nov. 13, 2018.
(Continued)

*Primary Examiner* — Lauren P Farrar
(74) *Attorney, Agent, or Firm* — Shay Glenn LLP

(57) ABSTRACT

A thrombectomy system and method of extraction of thrombus are disclosed. The thrombectomy system comprises a delivery catheter; an aspiration catheter, comprising an aspiration funnel, configured to be movably disposed within the delivery catheter in a retracted position and at least partially outside the delivery catheter in an extended and expanded position, the funnel comprising a non-permeable covering, the funnel being configured to adapt its shape and length to a surrounding blood vessel such that the funnel reduces blood flow through the blood vessel and lengthens as it narrows to retain a thrombus within the funnel; a clot-capture element configured to capture the thrombus and to be at least partially withdrawn with the captured thrombus into the funnel; and a microcatheter adapted to carry the
(Continued)

clot-capture element to the thrombus. The clot-capture element is movably disposed within the microcatheter in a retracted position. The microcatheter is movably disposed within the aspiration catheter.

21 Claims, 10 Drawing Sheets

(51) Int. Cl.
*A61F 2/95* (2013.01)
*A61M 25/00* (2006.01)

(52) U.S. Cl.
CPC ................ *A61B 2017/2212* (2013.01); *A61F 2002/9528* (2013.01); *A61M 2025/0042* (2013.01)

(58) Field of Classification Search
CPC ... A61B 2017/22094; A61B 2017/2215; A61F 2002/9528; A61F 2/013; A61F 2002/016; A61M 2025/0042
See application file for complete search history.

(56) References Cited

U.S. PATENT DOCUMENTS 4,921,478 A 5/1990 Solano et al.
5,011,488 A 4/1991 Ginsburg
5,092,839 A 3/1992 Kipperman
5,102,415 A 4/1992 Guenther et al.
5,190,561 A 3/1993 Graber
5,234,416 A 8/1993 MacCaulay et al.
5,449,373 A 9/1995 Pinchasik et al.
5,603,705 A 2/1997 Berg
5,605,530 A 2/1997 Fishell et al.
5,769,871 A 6/1998 Mers Kelly et al.
5,908,435 A 6/1999 Samuels
5,971,938 A 10/1999 Hart et al.
5,972,019 A 10/1999 Engelson et al.
6,066,149 A 5/2000 Samson et al.
6,159,230 A 12/2000 Samuels
6,190,303 B1 2/2001 Glenn et al.
6,402,771 B1 6/2002 Palmer et al.
6,514,273 B1 2/2003 Voss et al.
6,663,650 B2 12/2003 Sepetka et al.
6,695,858 B1 2/2004 Dubrul et al.
6,730,104 B1 5/2004 Sepetka et al.
6,752,819 B1 6/2004 Brady et al.
7,004,954 B1 2/2006 Voss et al.
7,108,677 B2 9/2006 Courtney et al.
7,578,830 B2 8/2009 Kusleika et al.
7,686,825 B2 3/2010 Hauser et al.
7,867,272 B2 1/2011 Niermann
7,993,302 B2 8/2011 Hebert et al.
8,088,140 B2 1/2012 Ferrera et al.
8,298,257 B2 10/2012 Sepetka et al.
8,679,142 B2 3/2014 Slee et al.
8,758,364 B2 6/2014 Eckhouse et al.
8,784,441 B2 7/2014 Rosenbluth et al.
8,858,497 B2 10/2014 Di Palma et al.
8,864,792 B2 10/2014 Eckhouse et al.
8,940,003 B2 1/2015 Slee et al.
8,984,003 B2 3/2015 Ahmed et al.
9,005,237 B2 4/2015 Eckhouse et al.
9,034,008 B2 5/2015 Eckhouse et al.
9,186,487 B2 11/2015 Dubrul et al.
9,463,035 B1 10/2016 Greenhalgh et al.
9,561,121 B2 2/2017 Sudin et al.
9,585,741 B2 3/2017 Ma
9,700,331 B2 7/2017 Grandfield et al.
9,844,381 B2 12/2017 Eckhouse et al.
9,861,783 B2 1/2018 Garrison et al.
10,285,720 B2 5/2019 Gilvarry et al.
10,292,804 B2 5/2019 Wang et al.
10,426,644 B2 10/2019 Shrivastava et al.
10,434,605 B2 10/2019 Feth et al.
11,013,523 B2 5/2021 Jacobi et al.
2002/0049493 A1 4/2002 Jang
2003/0009150 A1 1/2003 Pepin
2003/0023299 A1 1/2003 Amplatz et al.
2003/0212430 A1 11/2003 Bose et al.
2003/0212439 A1 11/2003 Schuler et al.
2004/0024416 A1 2/2004 Yodfat et al.
2004/0073243 A1 4/2004 Sepetka et al.
2004/0098099 A1 5/2004 McCullagh et al.
2004/0143317 A1 7/2004 Stinson et al.
2004/0167565 A1 8/2004 Beulke et al.
2004/0199201 A1 10/2004 Kellett et al.
2004/0199243 A1 10/2004 Yodfat
2004/0243102 A1 12/2004 Berg et al.
2004/0260333 A1 12/2004 Dubrul et al.
2005/0209678 A1 9/2005 Henkes et al.
2006/0058838 A1 3/2006 Bose et al.
2006/0064073 A1 3/2006 Schonholz et al.
2006/0155305 A1 7/2006 Freudenthal et al.
2006/0293744 A1* 12/2006 Peckham .................. A61F 2/07
156/227
2007/0118165 A1 5/2007 DeMello et al.
2007/0188165 A1 8/2007 Kitanaka et al.
2007/0198028 A1 8/2007 Miloslavski et al.
2007/0203559 A1 8/2007 Freudenthal et al.
2007/0208367 A1 9/2007 Fiorella et al.
2007/0213765 A1 9/2007 Adams et al.
2007/0276332 A1 11/2007 Bierman
2007/0288038 A1 12/2007 Bimbo
2008/0228209 A1 9/2008 DeMello et al.
2008/0269774 A1 10/2008 Garcia et al.
2008/0269798 A1 10/2008 Ramzipoor et al.
2009/0163846 A1 6/2009 Aklog et al.
2009/0198269 A1 8/2009 Hannes et al.
2010/0004607 A1 1/2010 Wilson et al.
2010/0030256 A1 2/2010 Dubrul et al.
2010/0222864 A1 9/2010 Rivelli et al.
2011/0160763 A1* 6/2011 Ferrera ............ A61B 17/12118
606/200
2011/0213297 A1 9/2011 Aklog et al.
2011/0213392 A1 9/2011 Aklog et al.
2012/0059309 A1 3/2012 Di Palma et al.
2012/0059356 A1* 3/2012 di Palma .......... A61B 17/12186
604/509
2012/0065660 A1 3/2012 Ferrera et al.
2012/0083868 A1 4/2012 Shrivastava et al.
2012/0114017 A1 5/2012 Bang et al.
2012/0116440 A1 5/2012 Leynov et al.
2012/0179181 A1 7/2012 Straub et al.
2012/0209311 A1 8/2012 Grandfield et al.
2012/0245671 A1 9/2012 Wainwright et al.
2013/0261638 A1 10/2013 Diamant et al.
2013/0325055 A1 12/2013 Eckhouse et al.
2013/0325056 A1 12/2013 Eckhouse et al.
2014/0052161 A1 2/2014 Cully et al.
2014/0074144 A1 3/2014 Shrivastava et al.
2014/0155908 A1 6/2014 Rosenbluth et al.
2014/0243885 A1 8/2014 Eckhouse et al.
2014/0277015 A1 9/2014 Stinis
2014/0371779 A1 12/2014 Vale et al.
2015/0112376 A1 4/2015 Molaei et al.
2015/0157346 A1 6/2015 Ferrera et al.
2015/0164666 A1 6/2015 Johnson et al.
2015/0231360 A1 8/2015 Watanabe et al.
2015/0359547 A1 12/2015 Vale et al.
2016/0081704 A1 3/2016 Jeon et al.
2016/0256255 A9 9/2016 Ma
2017/0065299 A1 3/2017 Gillespie et al.
2017/0071614 A1 3/2017 Vale et al.
2017/0079767 A1 3/2017 Leon-Yip
2017/0105743 A1* 4/2017 Vale ................ A61B 17/22032
2017/0119408 A1 5/2017 Ma
2017/0119409 A1 5/2017 Ma
2017/0215900 A1 8/2017 Lowinger et al.
2017/0215902 A1 8/2017 Leynov et al.
2017/0239444 A1 8/2017 Parker
2017/0303949 A1* 10/2017 Ribo Jacobi ..... A61B 17/12136

(56) References Cited

U.S. PATENT DOCUMENTS

2017/0333060 A1 11/2017 Panian
2018/0028209 A1 2/2018 Sudin et al.
2018/0064454 A1 3/2018 Losordo et al.
2018/0116684 A1 5/2018 Garrison et al.
2018/0126132 A1 5/2018 Heilman et al.
2018/0132876 A1 5/2018 Zajdat
2018/0206862 A1 7/2018 Long
2018/0318062 A1 11/2018 Sudin et al.
2018/0353196 A1 12/2018 Epstein et al.
2018/0361114 A1 12/2018 Chou et al.
2019/0110805 A1 4/2019 Ulm, III
2019/0167284 A1 6/2019 Friedman et al.
2019/0167287 A1 6/2019 Vale et al.
2019/0216476 A1 7/2019 Barry et al.
2019/0239907 A1 8/2019 Brady et al.
2019/0269425 A1 9/2019 Sudin et al.
2019/0269491 A1 9/2019 Jalgaonkar et al.
2019/0274810 A1 9/2019 Phouasalit et al.
2019/0298396 A1 10/2019 Gamba et al.
2019/0307471 A1 10/2019 Friedman et al.
2019/0336727 A1 11/2019 Yang et al.
2020/0000613 A1 1/2020 Shrivastava et al.
2020/0008822 A1 1/2020 Eckhouse et al.
2020/0085444 A1 3/2020 Vale et al.
2020/0205838 A1 7/2020 Walzman
2020/0281612 A1 9/2020 Kelly et al.
2021/0000582 A1 1/2021 Chomas et al.
2021/0059695 A1 3/2021 Haran et al.
2021/0068852 A1 3/2021 Spence
2021/0077134 A1 3/2021 Vale et al.
2022/0117614 A1 4/2022 Salmon et al.
2022/0211400 A1 7/2022 Cox et al.
2023/0127145 A1 4/2023 Arad Hadar et al.
2024/0374272 A1 11/2024 Villazón et al.
2025/0032134 A1 1/2025 Salmon et al.
2025/0134539 A1 5/2025 Garcia Sabido et al.
2025/0134540 A1 5/2025 Garcia Sabido et al.
2025/0160865 A1 5/2025 Arad Hadar
2026/0007420 A1 1/2026 Salmon et al.

FOREIGN PATENT DOCUMENTS

CN 104159525 A 11/2014
CN 107198554 B 2/2020
EP 1427087 A1 6/2004
EP 2662109 A1 11/2013
EP 3266391 A1 1/2018
ES 2341978 T3 6/2010
ES 2381099 T3 5/2012
GB 2498349 A 7/2013
JP 2005500138 A 1/2005
WO WO99/45835 A2 9/1999
WO WO02/087677 A2 11/2002
WO WO03/075793 A1 9/2003
WO WO2004/002564 A1 1/2004
WO WO2005/027751 A1 3/2005
WO WO2008/124567 A1 10/2008
WO WO2008/157202 A1 12/2008
WO WO2009/014723 A1 1/2009
WO WO2009/105710 A1 8/2009
WO WO2011/068924 A1 6/2011
WO WO2011/082319 A1 7/2011
WO WO2012/106657 A2 8/2012
WO WO2012/156924 A1 11/2012
WO WO2012/158269 A1 11/2012
WO WO2013/008233 A1 1/2013
WO WO2013/152327 A1 10/2013
WO WO2014/008460 A2 1/2014
WO WO2014/127389 A2 8/2014
WO WO2014/204860 A1 12/2014
WO WO2015/006782 A1 1/2015
WO WO2015/189354 A1 12/2015
WO WO2016/113047 A1 7/2016
WO WO2017/072663 A1 5/2017
WO WO2017/074290 A1 5/2017
WO WO2017/075544 A1 5/2017
WO WO2018/080590 A1 5/2018
WO WO2018/160966 A1 9/2018
WO WO2019/055311 A1 3/2019
WO WO2019/064306 A1 4/2019
WO WO2019/178131 A1 9/2019
WO WO2020/021333 A2 1/2020
WO WO2020/079082 A1 4/2020
WO WO2020/099386 A1 5/2020
WO WO2021/016213 A1 1/2021

OTHER PUBLICATIONS

Bouthillier et al.; Segments of the internal carotid artery: a new classification; Neurosurgery; 38(3); pp. 425-433; Mar. 1, 1996.
Rios Garriga et al.; U.S. Appl. No. 17/621,717 entitled "Delivery catheter device and system for accessing the intracranial vasculature," filed Dec. 22, 2021.
Berkhemer et al.; A randomized trial of intraarterial treatment for acute ischemic stroke; New England Journal of Medicine; 372; pp. 11-20; Jan. 1, 2015.
Ceretrieve; 3 pages; retrieved from the internet (http://trendlines.com/portfolio/ceretrieve/) on Sep. 13, 2018.
Duffy et al.; Novel methodology to replicate clot analogs with diverse composition in acute ischemic stroke; Journal of neurointerventional surgery; 9(5); pp. 486-491; May 1, 2017.
Fennell et al.; What to do about fibrin rich "tough clots"? Comparing the Solitaire stent retriever with a novel geometric clot extractor in an in vitro stroke model; Journal of neurointerventional surgery: 10(9); pp. 907-910; Sep. 1, 2018.
Mokin et al.; Stent retriever thrombectomy with the Cover accessory device versus proximal protection with a balloon guide catheter: in vitro stroke model comparison; Journal of neurointerventional surgery: 8(4); pp. 413-417; Apr. 1, 2016.
Arad Hadar; U.S. Appl. No. 17/235,764 entitled "Thrombectomy device, system and method for extraction of vascular thrombi from a blood vessel," filed Apr. 20, 2021.
Cortinas Villazon et al.; U.S. Appl. No. 17/274,973 entitled "A device and a thrombectomy apparatus for extraction of thrombus from a blood vessel," filed Mar. 10, 2021.
Salmon et al; U.S. Appl. No. 18/447,854 entitled "Thrombectomy system and method of use," filed Aug. 10, 2023.
Garcia Sabido et al; U.S. Appl. No. 18/546,190 entitled "An expandable clot mobilizer device for extraction of an occlusion from a blood vessel," filed Aug. 11, 2023.
Garcia Sabido et al.; U.S. Appl. No. 18/546,206 entitled "A self expandable medical device for advancement through vasculature to an expansion site in a blood vessel," filed Aug. 11, 2023.
Ros Fábrega et al.; U.S. Appl. No. 17/415,866 entitled "Loading device for loading a medical device into a catheter," filed Jun. 18, 2021.
Castano et al.; Unwanted detachment of the Solitaire device during mechanical thrombectomy in acute Ischemic stroke; Journal of neurointerventional surgery; 8(12); pp. 1226-1230; Dec. 1, 2016.
Penumbra Inc .; Recalls 3D revascularization device due to wire material that may break or separate during use; FDA Recall; retrieved from the internet (http:/web.archive.org/web/20200813123505/https:/www.fda.gov/medical-devices/medical-device-recalls/penumbra-inc-recalls-3d-revascularization-device-due-wire-material-may-break-or-separate-during-use).
Garcia-Sabido et al.; U.S. Appl. No. 18/040,492 entitled "A clot mobilizer device for extraction of an occlusion from a blood vessel," filed Feb. 3, 2023.
Garcia-Sabido et al.; U.S. Appl. No. 18/040,495 entitled "An elongated device with an improved attachment of its elements," filed Feb. 3, 2023.
Medtronic; Medtronic.com; The Solitaire Platinum Revascularization Device; Model Specifications; DC00079632 Rev A Mar. 2018; 1 page.

(56) References Cited

OTHER PUBLICATIONS

Ríos Garriga et al; U.S. Appl. No. 19/094,121 entitled "Delivery catheter device and system for accessing the intracranial vasculature," filed Mar. 28, 2025.

* cited by examiner

THROMBECTOMY SYSTEM AND METHODS OF EXTRACTING A THROMBUS FROM A THROMBUS SITE IN A BLOOD VESSEL OF A PATIENT

TECHNICAL FIELD

The present invention is directed, in general, to the field of medical devices. In particular, the invention relates to a thrombectomy system, which allows the removal of thrombi at the vascular level. The invention also relates to methods of extracting a thrombus from a thrombus site in a blood vessel of a patient. In some embodiments, the thrombectomy system includes a combination of an aspiration catheter and a clot-capture element.

BACKGROUND OF THE INVENTION

Acute ischemic stroke is a major cause of morbidity and mortality, with an annual incidence of 118 cases/100000 population and a mortality of 29 cases per 100000 population/year. These numbers position ischemic stroke as one of the main causes of death in developed countries together with cardiovascular diseases and cancer. In order to prevent or reduce complications related to this disease and to improve the prognosis of patients with ischemic stroke, it is necessary a clinical diagnosis to establish a proper reperfusion strategy in the shortest period of time. Until 2015 the treatment of choice for stroke was the recombinant tissue plasminogen activator (rtPA) administered intravenously 4.5 hours after symptom onset. However, this drug presents a narrow therapeutic window and not always gets recanalization. Consequently, intra-arterial recanalization therapy as mechanical thrombectomy is performed by means of various devices (Merci®, Penumbra®, etc.). The objective is to remove thrombus through aspiration, disruption or capture/extraction, viewed as a therapeutic option for patients who are not candidates for rtPA or in whom rtPA has failed. With the aim of improving the clinical outcomes achieved with these devices, stent retrievers appear to give this technique a more widespread use (Solitaire™, Trevo® and Revive).

Endovascular treatment of stroke has been performed since the 1990's. Its growth in the number of treated patients has been slow but constant. The main obstacle to its more widespread use is the necessity of a coordinated medical system at different levels to make it possible for patients to get to a medical center capable of administering these highly complex treatments within 6-8 hours of symptom onset.

Early strategies for the endovascular treatment of stroke provided local perfusion of a fibrinolytic agent through a catheter directly into the thrombus to dissolve blood clots. Beginning in the 2000 decade, a device that seemed to be more effective than intra-arterial fibrinolysis appeared. It was a spiral that unfolded around the thrombus, facilitating its extraction (the MERCI® retrieval system).

Starting in 2006, a new system became popular. A large-gauge catheter was designed to be advanced to the thrombus. The catheter was connected to a continuous aspiration pump to aspirate the thrombus (the Penumbra System®).

This system has evolved over the years, seeking to attain a catheter with an increasingly large diameter, able to navigate close to the thrombus.

In 2009, the use of stent retrievers started. Their use consists of crossing the thrombus with a microcatheter. Thereafter, the endoprosthesis is advanced through the microcatheter. Once the distal end of the microcatheter has reached the distal part of the thrombus, the endoprosthesis (stent retriever) is unsheathed, self-expanding through the thrombus and capturing it. It is recommended to wait a few minutes with the endoprosthesis expanded to enable proper engagement of the thrombus. The expanded stent is then withdrawn to drag the thrombus toward the catheter and out of the blood vessel. This last step can be done while aspirating through the catheter to try to reverse the blood flow in the vessel and to increase the likelihood of recovering the thrombus. In addition, when using a stent retriever, a guide balloon catheter is often used. This catheter only advances to the extracranial carotid (distant from thrombi located in the intracranial arteries).

Stent retrievers have entirely displaced the first-generation devices described above due to their high efficacy and speed. Several prospective randomized trials have recently demonstrated the marked superiority of stent retriever assisted mechanical thrombectomy with standard intravenous tissue plasminogen activator (IV tPA) thrombolysis over medical therapy (IV tPA) alone for revascularization of acute ischemic stroke in patients presenting with proximal large vessel occlusion.

However, the use of stent retrievers presents different as-yet unsolved challenges:

- Thrombus fragmentation. Stent retrievers may induce clot fragmentation causing distal embolization in a new territory (previously non-occluded vessels). Current aspiration catheters do not overcome this limitation either, since large-bore catheters' diameter is often smaller than the clot dimension.
- Prolonged revascularization time, as the fragmentation of the clot requires a multiple pass recanalization.
- Navigability issues in small/tortuous vessels.
- The long distance most of the clots must be dragged unprotected from the occlusion site to balloon guiding catheters, where the thrombus must be squeezed inside, leading again to the potential loss of the clot or the detachment of fragments from it.
- Once the clot has been moved out from the occlusion site, blood flow is restored and moving against the unprotected clot in the opposite direction of the retrieval movement, so any fragment or even the clot itself, if detached, will be generating a new occlusion, called secondary embolism.
- Even more, current systems for arresting the blood flow (mainly balloon catheters) must be placed far upstream from the thrombus, not deep in the neurovasculature at the thrombus site, which means that circulation is being restricted not only in the infarction zone but in a wider brain territory, leading to a cessation in blood flow in parts of the brain not affected by the clot itself.

Furthermore, despite advances in revascularization tools for large vessel occlusion presenting as acute ischemic stroke, a significant subset of clots remains recalcitrant to current strategies. Occlusions involving fibrin rich thrombi are more difficult to recanalize, often requiring a greater number of passes with the device than thrombi with higher red blood cell content (Fennell V S, et al. 2018). E.g. Calcified thrombus is harder and more difficult to remove than softer cardiogenic thrombi using either a stent retriever or an aspiration approach. A calcified lesion resists the stent retracting movement. Calcified thrombus are also difficult to remove by aspiration methods, since they have a harder consistency and tend to be densely packed within the vessel making it difficult to place the catheter tip within the calcified clot to maintain the vacuum needed for aspiration.

There are known some patent applications in this field. For example, US-A1-2018132876 discloses a system for removing a thrombus from a blood vessel including a stent retriever, a catheter configured to receive the stent retriever in a collapsed configuration, wherein the stent retriever is movable relative to the catheter, a sheath having a tubular body and defining a distal opening and a proximal opening, and a wire coupled to the stent retriever for positioning the stent retriever. The wire extends through the proximal opening and the distal opening of the sheath. The stent retriever is moveable relative to the sheath, and the distal opening of the sheath is sized to allow the stent retriever to be withdrawn into the sheath without substantially compressing the stent retriever.

WO-A1-2015006782 discloses a device and a method for intravascular treatment of an embolism. The device comprises a clot treatment device that includes a support member configured to extend through a delivery catheter and a plurality of clot engagement members positioned about the circumference of a distal portion of the support member. The clot engagement members can be configured to penetrate clot material along an arcuate path and mechanically macerate clot and release embolic particles when re-sheathed into the delivery catheter.

US-A1-2017119408 discloses a clot removal device comprising an expandable treatment member having a distal tip and a proximal end, a delivery wire having a distal end coupled to the proximal end of the expandable treatment member, and a flow restrictor carried along the delivery wire at a location that is separate and proximal from the expandable treatment member. The flow restrictor has a body with a distal section and a proximal section, the distal section being covered and the proximal section being uncovered. The expandable treatment member is moveable relative to the flow restrictor, and can be retracted into the distal section.

DESCRIPTION OF THE INVENTION

A problem to be solved by the present invention is to improve the efficacy of the currently used clot-capture devices, and particularly, stent retrievers. This is particularly interesting for the capture of hard clots such as fibrin rich clots.

The present invention according to a first aspect provides a thrombectomy system. The proposed thrombectomy system comprises: a delivery catheter configured to be advanced through vasculature of a patient to a thrombus site within a blood vessel; an aspiration catheter adapted to apply suction to an expandable aspiration funnel extending from a distal end of the aspiration catheter, the aspiration funnel being configured to be movably disposed within the delivery catheter in a retracted position in a compressed state (in the delivery configuration) and at least partially outside the delivery catheter in an extended and expanded position (also referred in this description as "in a deployment configuration"), the aspiration funnel comprising a non-permeable covering, a diameter of a distal end of the aspiration funnel being greater in the extended and expanded position than in the retracted position, the aspiration funnel being configured to adapt its shape and length to an inner wall of the blood vessel such that the aspiration funnel reduces blood flow through the blood vessel and lengthens as it narrows to retain a thrombus within the aspiration funnel; a clot-capture element configured to be able to capture the thrombus and to be at least partially withdrawn with the captured thrombus into the aspiration funnel; and a microcatheter adapted to carry the clot-capture element to the thrombus site.

According to the invention, particularly, the clot-capture element is movably disposed within the microcatheter in a retracted position. Likewise, the microcatheter is movably disposed within the aspiration catheter. Moreover, the different elements of the thrombectomy system can be moved together or separately. In an embodiment, the interconnection between the elements is through hemostatic valves.

A suitable thrombectomy device for use for the purposes of the invention is described in the patent application WO2016113047A1 which is herein incorporated by reference in its entirety.

In a particular embodiment, the delivery catheter, the aspiration funnel, the microcatheter and the clot-capture element are oriented on the same axis, are coaxially configured and movable to each other independently.

In a particular embodiment, the aspiration funnel is self-expandable.

The thrombectomy system/apparatus of the invention can be used in the neurovasculature or in the peripheral vasculature and is particularly suited to navigate to the desired location and provide a concrete sealing where it is most needed, thus avoiding development of secondary thrombi for instance. Its design allows the introduction of a retrieval device that actuates as a clot mobilizer to remove a thrombus by dragging it into the funnel mouth. The approach of the invention consists in guiding the thrombectomy device to a position close to the thrombus and to retrieve it by means of aspiration combined with a mechanical action. The aspiration funnel is a self-expandable covered stent operated with the use of a catheter (e.g. a guiding catheter) that enables its navigation and positioning. Moreover, the catheter is intended to maintain the vacuum from its proximal end, where the vacuum is generated by an interventionist (e.g., with a syringe), to the vicinity of the thrombus at the distal end of the catheter.

This covered aspiration funnel can be in retracted or extended configurations, the diameter of the aspiration funnel being bigger in the extended configuration than in the retracted configuration. Additionally, the aspiration funnel is designed not to cause damage to the intracranial or peripheral artery. Its design is intended to adjust to the diameter of the artery and, as a result, to restrict the blood flow which is one of the most important characteristics of the described system for the prevention of distal embolism. Distal embolism is a typical clinical complication when a stent retriever crosses a clot or during the extraction process.

In an embodiment, the expansion behavior of the aspiration funnel is due to the Nitinol material from which it is formed, thanks to its shape memory properties and super elasticity. Shape memory refers to the ability to undergo deformation and then recover its original shape by heating the material above its "transformation temperature". In combination with super elasticity, Nitinol presents the right characteristics to position to different diameters and geometries of the vessel.

Further, advantages of the thrombectomy system can be summarized as follows: The aspiration funnel, a self-expandable stent (formed, e.g., from Nitinol) sealed with a film of polymeric material, upon deployment expands and mimics the blood vessel dimensions. Advantageously, the large mouth of the funnel together with the clot-capture element is able to aspirate the entire thrombus without fragmenting it and also allocates the clot perfectly during the removal procedure. The loss of the clot due to the long distance from the occlusion site to the exit and also due to the big size of the clot (difficult to catch by the clot-capture element) is also prevented. The system is able to restrict blood flow in the vessel and, as result, increases the aspiration power of the system and reduces further clinical side complications, mainly distal embolism. Another key feature of the system is that, as the flow is not stopped at carotid level, but directly at the thrombus site, only a particular arterial branch is affected, not the entire hemisphere, thus increasing the safety of the overall procedure. In summary, the thrombectomy system of the invention offers a clear advantage respect other marketed or ready-to be marketed devices.

The clot-capture element in the present description is understood as a device able to interact with the clot in order to capture it and retrieve it from the blood stream. This definition includes the following categories without being limiting for the present invention:

- Coil retriever system. This category includes first generation of clot-capture elements like the Merci® retriever system, which is a helically-tapered cork screw like catheter tip. The second generation incorporates a helical coil at 90° with respect to the proximal catheter along with added filaments. And the third generation is a hybrid design of non-tapered, non-angulated filamented helical coil to allow for maximal clot retention.
- Stent retriever, which is in this description a device normally with a metallic mesh which operates through a metallic pusher, able to capture the clot by retrieving it within its struts. Examples of stent retrievers include the following:
  - Solitaire FR (Medtronic Neurovascular)
  - Trevo™ XP ProVue Retrieval System (Stryker)
  - Embotrap (Neuravi)
  - Revive PV (DePuy Synthes)
  - pReset (Phenox)
  - Eric (Microvention)
  - MindFrame Capture LP System (Covidien)
  - APERIO (Acandis GmbH)
  - Catch (Balt Extrusion)
  - Tigertriever (Rapid Medical)
  - Stream (Perflow Medical)
  - Jrecan
  - 3D Revascularization device (Penumbra)
  - Neva (Vesalio)
  - Versi (Neurovasc Technologies)
- Other types of clot-capture elements include:
  - Golden Retriever (Amnis)
  - Triticum Medical
  - ClotTriever thrombectomy device (Inari Medical)
  - Dais-e (Mivi Neuroscience)
  - Navimax (Intratech Medical)
  - ThromboWire (Capture Vascular Systems)

In a particular embodiment, the clot-capture element is a stent retriever device. More particularly the stent retriever device has closed cells and a continuous scaffold like Solitaire™ revascularization device or Trevo Stentriever™.

In an embodiment, the aspiration funnel comprises a segment defining a distal end and a proximal end and is formed by a mesh of at least two sets, equal or different, of helicoidal filaments (or wires) turning respectively in opposite directions and being intertwined. The mesh comprises a first tubular section, particularly of a uniform diameter, and a second tubular section, adjacent to the first section, having a diameter smaller than that of the first tubular section.

The mesh of the first section has helicoidal filaments with a braiding angle (β) adapted to provide outward radial forces, i.e. pressure, higher than in the second section, such that the first section becomes better appositioned, or overlapped, against the inner wall of the blood vessel. The first section may comprise closed loops at the distal end configured to act as a spring, such that the radial forces in the first and second end portions of the first section are higher than in an intermediate portion of the first section.

The straight shape of the first section of the aspiration funnel creates a space which will accommodate the thrombus once it has been aspirated. The first section is adaptable to the vessel geometry and its outer surface overlaps the inner wall of the blood vessel.

Particularly, the second section comprises two sub-sections, a first sub-section and a second sub-section. The first sub-section has a cone-shape (or funnel-shape) and comprises a braiding angle (α) that change at its proximal and distal ends to provide radial strength to maintain the conical shape and to reduce the proximal blood flow during the removal of the thrombus. The second sub-section comprises a tubular uniform diameter configured to provide a connection to the aspiration catheter.

The aspiration funnel can be produced in different sizes. In an embodiment, the first section is longer than the second section. In an embodiment, the first section comprises a length ranging between 4 and 40 millimeters and an outer diameter ranging between 3.5 and 6 millimeters, and the second sub-section comprises a length ranging between 1 and 10 millimeters and an outer diameter ranging between 1 and 2 millimeters. Moreover, the braiding angle (α) of the first sub-section is comprised between 15 and 45 degrees with regard to a longitudinal axis of the aspiration funnel. This angle favors having more radial force thereby stopping the flow, but at the same time that there is a seal of the blood vessel it also has to allow the aspiration funnel to be compressed.

In another embodiment, the non-permeable covering of the aspiration funnel comprises a polymer, for example silicone or polyurethane.

The helicoidal filaments of the mesh can be made of a metal, a metal alloy or a composite including, among others, Nitinol or Nitinol/Platinum, or also Niti #1-DFTR® (Drawn Filled Tube), with a percentage of Platinum from 10% to 40%; in particular with 20% Platinum (Niti #1-DFTR®-20% Pt). The helicoidal filaments are adapted to become more longitudinally aligned as the aspiration funnel lengthens and narrows.

The helicoidal filaments, in an embodiment, comprise a number ranging between 12 and 48 filaments, and particularly between 18 and 24 filaments. In this case, the filaments have a cross section comprised in a range between 40 and 60 μm, and particularly 50 μm, and the braiding angle (β) of the filaments with regard to the longitudinal axis of the aspiration funnel is comprised between 50 and 65 degrees for the first section, and between 15 and 50 for the second sub-section.

The aspiration funnel may also include or have attached thereto one or more sensors to provide information thereof. For example, a lighting sensor or sensors may provide information of whether the aspiration funnel is in the retracted position within the delivery catheter or in the extended and expanded position. The sensor(s) can alternatively, or additionally, provide information on whether the aspiration funnel is well extended and expanded, on whether the thrombus is in or out, about the composition of the thrombus, or about the position of the funnel in relation to the blood vessel. Alternatively, the sensor(s) may include a piezoelectric sensor providing information about the radial forces in each of the different sections or subsections of the aspiration funnel. Alternatively, the sensor(s) may provide information to distinguish between blot obstruction and intracranial atherosclerotic disease.

Advantageously, the aspiration funnel can also comprise at least one radiopaque marker at its distal end and/or other strategic point(s) of the mesh which allow a physician to know the precise location of the aspiration funnel while using fluoroscopy.

Another aspect of the invention relates to a method of extracting a thrombus from a thrombus site in a blood vessel of a patient, the method comprising:

advancing a delivery catheter through vasculature toward the thrombus site;

placing a distal end of the delivery catheter proximal to the thrombus in the blood vessel;

advancing an aspiration catheter within the delivery catheter, an aspiration funnel extending distally from the aspiration catheter;

moving the aspiration catheter and delivery catheter with respect to each other to place the aspiration funnel outside of the delivery catheter proximal to the thrombus;

expanding the aspiration funnel into contact with inner walls of the blood vessel, thereby reducing blood flow past the aspiration funnel;

advancing a clot-capture element distally through the aspiration funnel toward the thrombus;

deploying the clot-capture element to capture the clot;

moving the clot-capture element and thrombus proximally toward the aspiration funnel;

applying suction through the aspiration catheter to the aspiration funnel to aspirate the thrombus at least partially into the aspiration funnel; and moving the aspiration funnel and the thrombus proximally within the vasculature, the aspiration funnel adapting its shape and length to a surrounding blood vessel by lengthening as it narrows to retain the thrombus within the aspiration funnel.

It should be noted that the steps of the proposed method can be performed in any order. In particular, the step of applying suction can be performed either before or after the step of moving the aspiration funnel and the thrombus proximally within the vasculature.

Optionally, the method may also comprise advancing a microcatheter within the aspiration catheter, the clot-capture element being disposed within the microcatheter. Moreover, the method may also comprise moving the microcatheter and clot-capture device with respect to each other to place the clot-capture device outside of the microcatheter; and expanding the clot-capture device.

In an embodiment, the expanding of the clot-capture device comprises allowing the clot capture device to self-expand.

In an embodiment, advancing a microcatheter comprises advancing a distal end of the microcatheter through the thrombus.

Optionally, the method may also comprise moving the clot-capture device proximally at least partially into the aspiration funnel.

In an embodiment, expanding the aspiration funnel comprises allowing the aspiration funnel to self-expand.

In an embodiment, the aspiration funnel comprises a mesh of at least two sets of intertwined helicoidal filaments turning respectively in opposite directions, the method further comprising moving the two sets of helicoidal filaments to a more longitudinally aligned position as the aspiration funnel lengthens and narrows.

Another aspect of the invention relates to a method of extracting a thrombus from a thrombus site in a blood vessel of a patient, the method comprising:

advancing a clot-capture element distally through vasculature toward the thrombus site; and particularly, the clot-capture element is self-expanded toward the thrombus site;

advancing a delivery catheter through vasculature toward the thrombus site;

placing a distal end of the delivery catheter proximal to the thrombus in the blood vessel;

advancing an aspiration catheter within the delivery catheter, an aspiration funnel extending distally from the aspiration catheter;

moving the aspiration catheter and delivery catheter with respect to each other to place the aspiration funnel outside of the delivery catheter proximal to the thrombus;

expanding the aspiration funnel into contact with inner walls of the blood vessel, thereby reducing blood flow past the aspiration funnel;

moving the clot-capture element and thrombus proximally toward the aspiration funnel;

applying suction through the aspiration catheter to the aspiration funnel to aspirate the thrombus at least partially into the aspiration funnel; and moving the aspiration funnel and the thrombus proximally within the vasculature, the aspiration funnel adapting its shape and length to a surrounding blood vessel by lengthening as it narrows to retain the thrombus within the aspiration funnel.

By advancing the clot-capture element distally through vasculature toward the thrombus site, the clot-capture element is used as an anchor element, thus pushability/navigability of the delivery catheter is enabled.

BRIEF DESCRIPTION OF THE DRAWINGS

The previous and other advantages and features will be more fully understood from the following detailed description of embodiments, with reference to the attached figures, which must be considered in an illustrative and non-limiting manner, in which.

DETAILED DESCRIPTION OF PARTICULAR EMBODIMENTS

Figure 1:
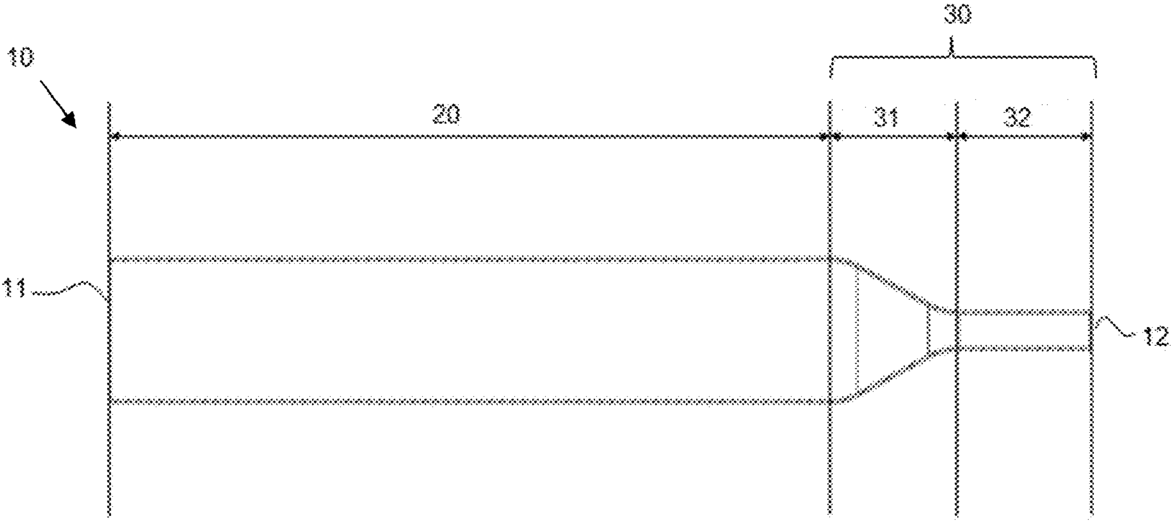
FIG. 1 schematically illustrates the different sections included in the aspiration funnel for extraction of thrombus from a blood vessel, according to an embodiment of the present invention.
Figure 2:
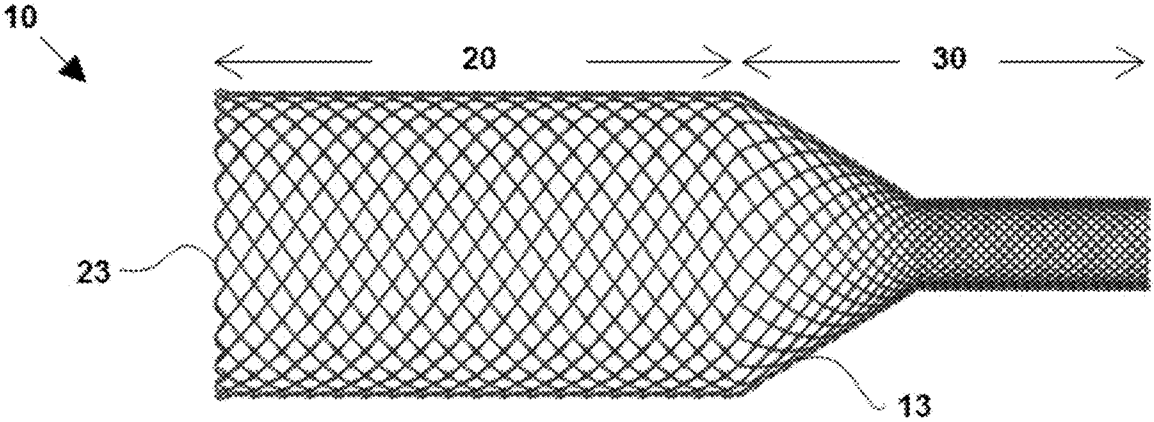
FIG. 2 illustrates the mesh included in the different tubular sections of the aspiration funnel having a lower mesh density in the first section than in the second section.

FIGS. 1 and 2 show particular embodiments of the aspiration funnel 1 included in the proposed thrombectomy system/apparatus (or ANCD) for extraction of thrombus from a blood vessel. The aspiration funnel 1 includes a segment 10 which is self-expandable and defines a distal end 11 and a proximal end 12 and can adapt its shape to a surrounding blood vessel from a retracted position in a compressed state, for example inside a carrier such a delivery catheter 3, to an extended/expanded position, once coming out of the delivery catheter 3, to be appositioned against the inner wall of a blood vessel to receive and retain a thrombus THR.

As shown in FIG. 2, the segment 10 comprises a mesh 13 having two sets of helicoidal filaments turning respectively in opposite directions and being intertwined. The mesh 13 in an embodiment can follow a diamond-type structure or a regular structure. The density of the mesh 13 defines the elasticity of the segment 10. As detailed in Table 1 the mesh angle (or braiding angle (β)) with regard to a longitudinal direction can be variable.

The helicoidal filaments can be made of a metal (including metal alloys), polymers, a composite including Nitinol or Nitinol/Platinum, or also DFT® (Drawn Filled Tube), among other materials having suitable mechanical properties.

As can be seen in the FIGS. 1 and 2, the mesh 13 defines two distinct tubular sections, a first section 20 and a second section 30. Particularly, the second section 30 comprises two sub sections, a first sub section 31 and a second sub section 32.

As can be seen in FIG. 2, in this particular embodiment, the end portion of the first section 20 at the distal end 11 comprises closed loops 23 facilitating the expansion of the segment 10 once it comes out of the cited delivery catheter 3. Moreover, these closed loops 23 act as a spring or fixing point by limiting the movement between the helicoidal filaments and thus increasing the outward radial force. The closed loops 23 also provide a smooth distal end to reduce possible vessel damage and improve navigability of the aspiration funnel 1 within the blood vessel. The rest of the first section 20 creates the space which will accommodate the thrombus THR once it has been aspirated. The first section 20 is adaptable to the vessel geometry and, because of its configuration (e.g., diameter and braiding angle β), provides outward radial forces higher than in the second section 30 so that the segment 10 is better appositioned against the inner wall of the vessel. The radial forces in the end portions of the first section 20 are particularly higher than in an intermediate portion thereof, e.g., because of the spring action of closed loops 23. Alternatively, the radial forces in the first section 20 could be uniformly distributed along all its generatrix.

The first sub-section 31 (or portion of the second section 30 adjacent to the first section 20) is cone-shaped or funnel-shaped. Because of its shape, this sub-section 31 has features enabling it to withstand the blood pressure without collapsing. In the illustrated embodiment, the braiding angle (α) change at the proximal and distal ends of sub-section 31 provide radial strength to maintain the conical shape. The braiding angle (α) change at the distal end of sub-section 31 also works with the closed loops 23 to maintain first section 20 in an open position and create the space for the thrombus THR. The covering over sub-section 31 stops the blood flow during the capture and removal of the thrombus THR and protects the captured thrombus THR during the withdrawal of the segment 10 to the delivery catheter 3. This sub-section 31 is also the transition from the larger diameter of section 20 to the smaller diameter sub-section 32 for connection to an aspiration catheter 2 (see FIG. 5), or alternatively to a hypotube.

The second sub-section 32 (or portion of the second section 30 adjacent to proximal end 12) has a tubular uniform diameter and provides the connection to the aspiration catheter 2. In some embodiments, the aspiration catheter 2 is a PTFE-lined braided catheter covered by an outer jacket. The aspiration catheter's braid and liner extend distally from the outer jacket. A layer of polymer material may be placed around the protruding braid and liner, and a mandrel may be placed within the braid and liner. Thereafter, the second sub-section 32 of segment 10 may be placed over this polymer section, and another layer of polymer may be placed over the mesh of subsection 32. This outer layer of polymer material is then melted so that polymer flows through the cells of the mesh 13, the mandrel is removed, and a smooth surface is left over the entire aspiration catheter 2. This attachment approach adds structure and stiffness to the attachment section of the aspiration catheter 2, so it should be as short as possible without compromising the integrity of the attachment of segment 10 to the aspiration catheter 2.

Other techniques of connecting segment 10 to the aspiration catheter 2 may be used, as understood by skilled artisans. For example, in other embodiments, if the aspiration catheter 2 is a metal hypotube, the mesh 13 of the sub-section 32 is welded to a Nitinol ring. This ring is welded directly to the hypotube. Alternatively, a Stainless-steel ring can be glued to the mesh 13 of the sub-section 32. Then, the Stainless-steel ring is welded to the hypotube. Another option is to directly mesh the segment 10 over a perforated ring so that the filaments pass through the holes.

When the segment 10 is compressed inside the delivery catheter 3, segment 10 elongates to move the helicoidal filaments toward a longitudinal alignment so as to reduce the spring effect and to facilitate the movement of segment 10 within the delivery catheter 3 by reducing friction effects and by increasing pushability. The pushability of the segment 10 inside the delivery catheter 3 is related to the navigability of the segment 10 within the arteries.

The mesh angle or braiding angle (β) allows the mesh 13 to be adapted to a curve of the blood vessel, avoiding the kinking and creating a free space inside the mesh for unobstructed suction.

Figure 3:
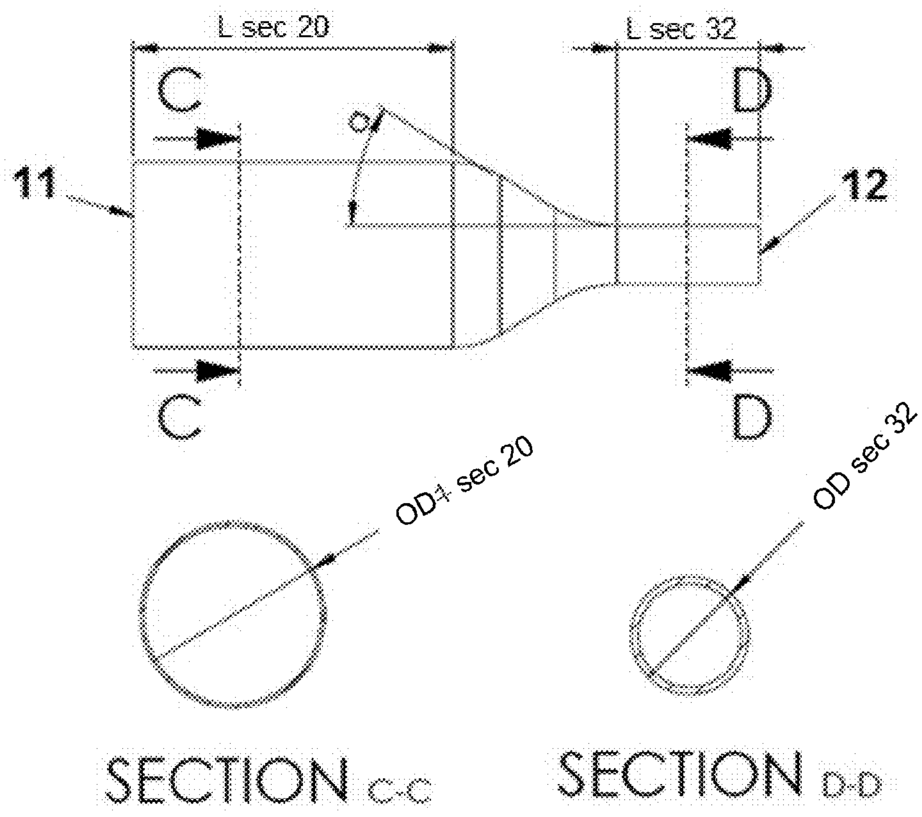
FIG. 3 schematically illustrates some of the main specifications of the aspiration funnel.

With reference now to FIG. 3 therein are illustrated some of the main specifications of the aspiration funnel 1 according to an embodiment. Table 1 indicates the main specifications of the aspiration funnel 1. Table 2 indicates the measuring method used for calculating such parameters.

TABLE 1

| Main specifications of the aspiration funnel | | | | | |
|---|---|---|---|---|---|
| | | Example | Range | Big Ref. | Small Ref. |
| Shape parameters | OD sec 20 [mm] | 6 | 3.5--6 | 5.2 | Approx. 4.1 |
| | OD sec 32 [mm] | catheter OD | 1--2 | 1.65 | 1.65 |
| | L sec 20 [mm] | 15 | 4--40 | 9 | 4-8 |
| | α sec 31 [°] | 45 | 15--45 | 31 | 20 |
| | L sec 32 [mm] | 2 | 1--10 | 3.5 | 3 |
| Braiding parameters | Wire OD [μm] | 50 | 40--60 | 51 | 51-58 |
| | Wire number | 48 | 24--48 | 48 | 24-36 |
| | β sec 20 [°] | 60 | 50--65 | 55 | 65 |
| | β sec 32 [°] | 20 | 15--50 | 45 | 45 |

Table 1 shows the parameters for particular embodiments. In an embodiment, the parameters of the aspiration funnel 1 are such indicated in Table 1 for a big blood vessel ("Big Ref.") of e.g. 4.5 mm diameter, such as the final part of the carotid or the carotid siphon. In another embodiment, the parameters of the aspiration funnel 1 are such indicated in Table 1 for a small blood vessel ("Small Ref.") of e.g. 2.5 mm diameter, such as the Internal Carotid Artery (ICA) or the Middle Cerebral Artery (MCA).

TABLE 2

| Measuring methods used for calculating the different parameters. | |
|---|---|
| Parameter | Measuring method |
| OD sec 20 [mm] | The mandrel on which the aspiration funnel is meshed is measured. It is a solid piece with the same shape as the stent. The final diameter is determined by measuring the diameter of the solid piece and adding 4 times the diameter of the helicoidal filaments/wires. |
| OD sec 32 [mm] | Same as before |
| L sec 20 [mm] | Same as before |
| α sec 31 [°] | Same as before |
| L sec 32 [mm] | Once the aspiration funnel has been meshed, it is placed on a tool that determines where the excess length should be cut. |
| Wire OD [μm] | It is measured with a precision measuring instrument. |
| Wire number | Alternative 1: Counting the number of distal loops and multiplying by 2<br>Alternative 2: Counting the number of reels used for meshing |
| β sec 20 [°] | Alternative 1: Measuring the number of wire crossings in a given length measured in the axial direction.<br>Alternative 2: If the mandrel is manufactured with grooves so that during the meshing the wires are inserted inside, and the manufacturing is improved, it is simply measured that the mandrel is manufactured with the appropriate parameters. |
| β sec 32 [°] | Same as before. |

As mentioned, the aspiration funnel 1 may be in two configurations: in a retracted form (or compressed state) inside the delivery catheter 3 while approaching the thrombus site, and in an extended and expanded (deployed) form when there is no interaction with the delivery catheter 3 or the blood vessel. The parameters specified herein relate to the aspiration funnel 1 in its natural (relaxed) form; i.e. extended and expanded (deployed) position.

The segment 10 may include radiopaque markers made of platinum, tungsten, barium derivatives, gold, iridium, among others, at its distal end 11 and/or other strategic points within the mesh 13 which allow a physician to know the precise location of the aspiration funnel 1 while using fluoroscopy. The radiopaque material can be deposited on the helicoidal filaments once manufactured (if the aspiration funnel 1 has a coating, the material may also be dispersed on the surface of the coating). Alternative possibilities to confer radiopacity to the segment 10 are using helicoidal filaments of different material and opacity grade (e.g. Nitinol and Platinum). In a particular embodiment, Nitinol wires with a Platinum core are used. Likewise, the delivery catheter 3 may also include radiopaque markers.

Moreover, the segment 10 may have a coating, for example covering the first section 20 only or covering the whole segment 10. In the embodiments of FIGS. 1 and 2, although not seen, the coating goes from the closed loops 23 to sub-section 32. In one embodiment, the coating is applied about attachment of segment 10 to the aspiration catheter 2 by dipping segment 10 into a liquid polymer, therefore allowing the polymer to solidify. Optionally, a mandrel may be disposed inside the mesh 13 of segment 10 when it is dipped into the polymeric coating material. Alternatively, the coating material may be sprayed onto the mesh 13. In other alternative embodiments, the coating may be applied before attaching segment 10 to the aspiration catheter 2. In such embodiments, the coating does not reach the proximal end 12 of sub-section 32, but there is an uncoated space between the helicoidal filaments, leaving them free to allow assembly with the aspiration catheter 2.

The coating prevents damage to the arteries, avoiding direct contact with the helicoidal filaments. Moreover, the coating provides a watertight compartment so that the thrombus THR can be sucked in and protected during removal. In an embodiment, to apply the coating, the mesh 13 is attached to the delivery catheter 3 and then the coating is applied.

An interior or exterior glaze can be also applied to the coating to improve its properties. By applying a hydrophilic or hydrophobic coating to the exterior surface of the segment 10, the exterior surface can be more easily displaced into the carrier and through the blood vessel by reducing the coefficient of friction. In the same way, by applying a treatment in the interior surface of the segment 10 an adhesion effect that retains the thrombus THR once it is inside can be achieved.

The coating is made of an elastic material. In one particular embodiment, the aspiration funnel 1 coating is silicone. Alternatively, polyurethanes or other types of plastic materials can be used. A blend of polyurethane and silicone may also be employed.

To achieve the double behavior of the coating (lubricious on the exterior surface of segment 10 and tacky or rough inside), the coating can be treated by the addition of a material as explained or can have constitutively such features by the structure of the mesh itself.

The coating can include holes to avoid collapse of the segment 10. Such holes may be formed after the coating has been applied by perforating the coating.

Figure 4:
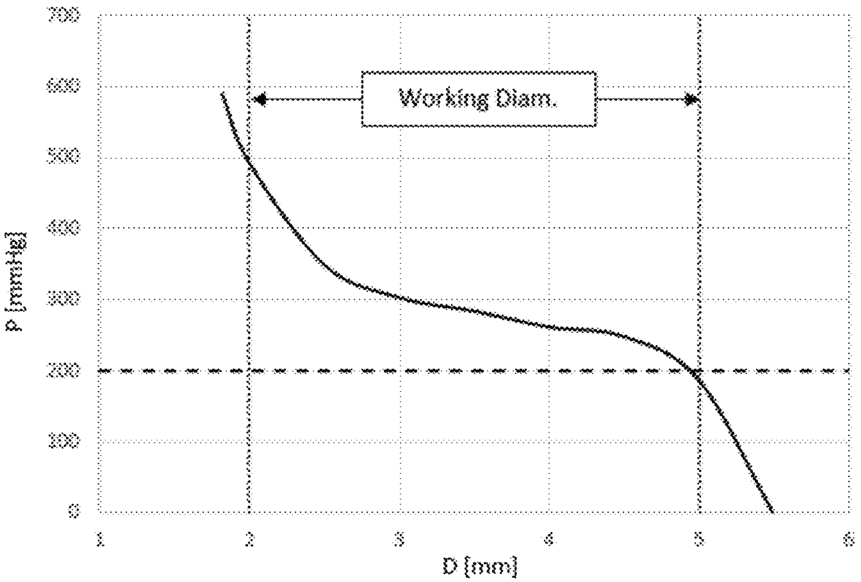
FIG. 4 is a graph showing Ideal pressure vs. diameter curve of the aspiration funnel.

The dimensions of segment 10 depend on the dimensions of the blood vessel in which it will be used to capture a thrombus THR. The dimensions of the sub-sections of segment 10 and the braid angles of the mesh help segment 10 provide a reduced radially outward force when compressed into the delivery catheter 3 and sufficient outward force when expanded to avoid collapse from the blood pressure. FIG. 4 illustrates a possible work curve of one embodiment of the segment 10. Y-axis defines the device pressure (mmHg) whereas X-axis defines the diameter of the arteries (mm). The horizontal dotted line marks the blood pressure limit. In some embodiments, the diameter range of the arteries in which the aspiration funnel 1 of this invention may be used is 2 to 5 mm. The segment 10 is designed so that it can expand without being blocked by the artery working in a standard range of 2 to 5 mm and so that it can cope with a blood pressure greater than 200 mmHg. As shown by FIG. 4, this particular embodiment is not designed to be compressed to a diameter less than 2 mm. Compression of the segment 10 within the delivery catheter 3 may result in radially outward forces high enough to inhibit advancement of the aspiration funnel 1 within the carrier.

Some embodiments of the invention may be automated for used in traditional (hospital) and non-traditional (nursing home, assisted care facility) environments which may allow for greater deployment and usage of the ANCD and hasten the removal of thrombus THR, thus significantly improving patient outcomes, as flow may be restored (e.g., to critical areas of the brain) within much shorter times. One such automated device is illustrated in WO2016/113047.

In use of the ANCD, segment 10 and the aspiration catheter 2 to which it is attached are advanced through the delivery catheter 3 to a thrombus site within a blood vessel of the patient. During advancement in the delivery catheter 3, the segment 10 is in a delivery configuration in which the first and second sets of helicoidal filaments form a first distally facing angle with respect to each other. When segment 10 emerges from the delivery catheter 3, it begins to self-expand to a deployment configuration. In embodiments in which the mesh 13 forms closed loops at the distal end of segment 10, the spring action of the closed loops of the helicoidal filaments helps the first section 20 expand into apposition with the blood vessel proximate to the thrombus site. In the deployment configuration, the first and second sets of helicoidal filaments form a second distally facing angle less than the first angle (i.e., the filaments are less longitudinally aligned in the deployment configuration than they were in the delivery configuration). Sub-section 31 also self-expands to a conical or funnel shape. The distal end of sub-section 31 helps support the proximal end of section 20 in its deployment configuration.

The coating on the outside of sub-section 31 and section 20 reduce blood flow to the thrombus site. The optional holes through the coating permit a small amount of blood to pass through the aspiration funnel 1 to avoid collapse of sub-section 31 caused by the blood pressure and also by the difference of pressure between the blood pressure (externally) and the vacuum applied (internally). Once blood flow has been reduced, suction may be applied through the catheter 2 to the interior spaces of sub-section 31 and section 20 to aspirate the thrombus THR into section 20. Aspiration funnel 1 capturing the thrombus THR may then be removed from the patient. In the capture configuration (i.e. when the thrombus THR is inside), the first and second sets of filaments form a third distally-facing angle less than the first distally-faced angle (i.e., the filaments become more longitudinally aligned) as the aspiration funnel 1 assumes a longer and smaller diameter shape.

Figure 5:
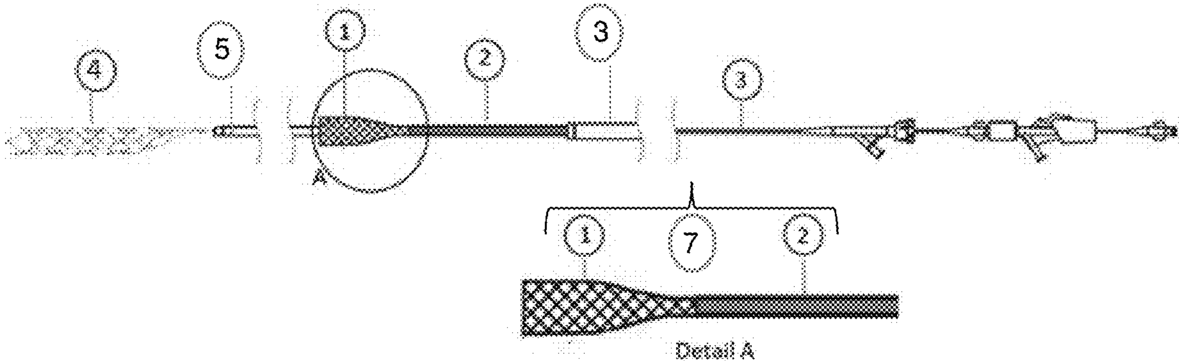
FIG. 5 is a scheme of the proposed thrombectomy system.

With reference to FIG. 5, therein it is illustrated a scheme of an expanded configuration of the proposed ANCD, which in this particular embodiment includes an aspiration funnel 1, an aspiration catheter 2 connected to the aspiration funnel 1, a delivery catheter 3; a clot-capture element 4 and a microcatheter 5. Detail A shows a scheme of an expandable-tip aspiration catheter 7 comprising the aspiration funnel 1 and the aspiration catheter 2.

Figure 6:
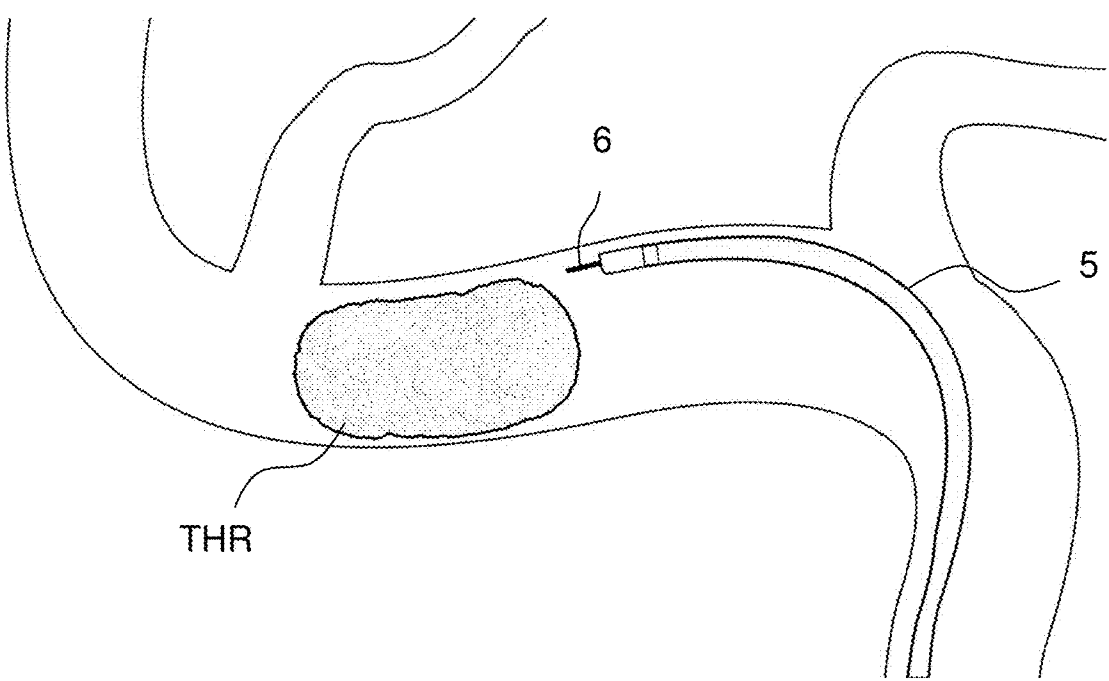
FIGS. 6-13 show the steps of a method of extracting a thrombus from a thrombus site in a blood vessel of a patient using the thrombectomy system of the invention.
Figure 7:
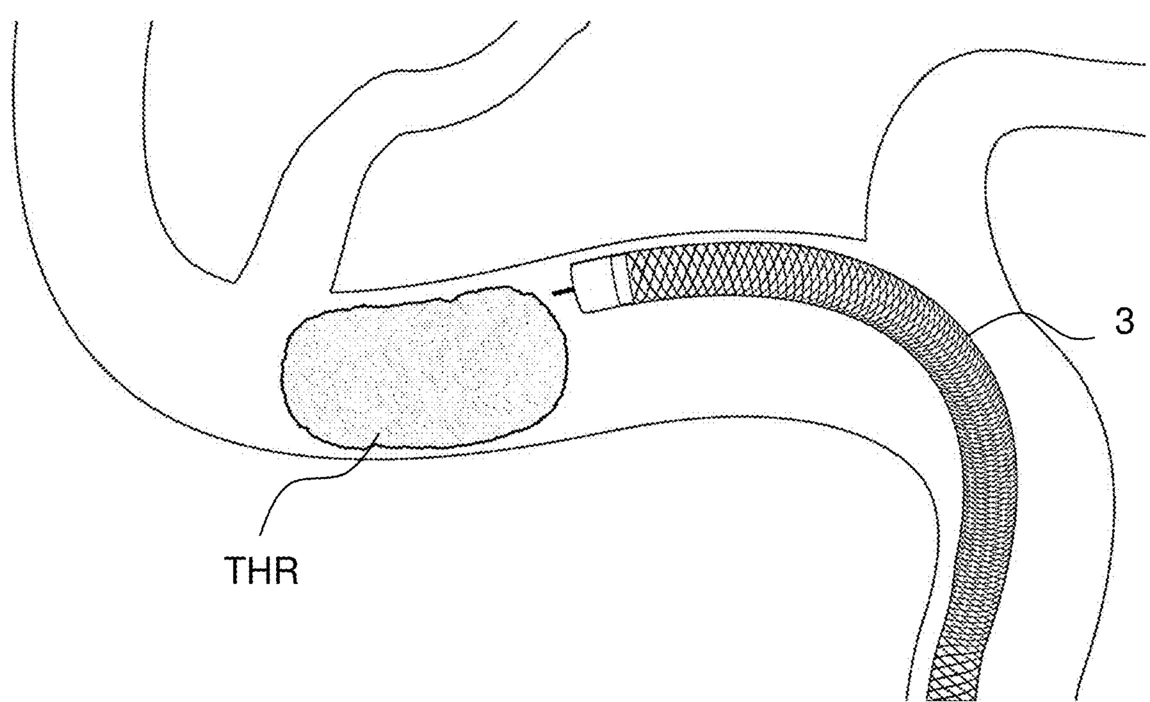
Figure 8:
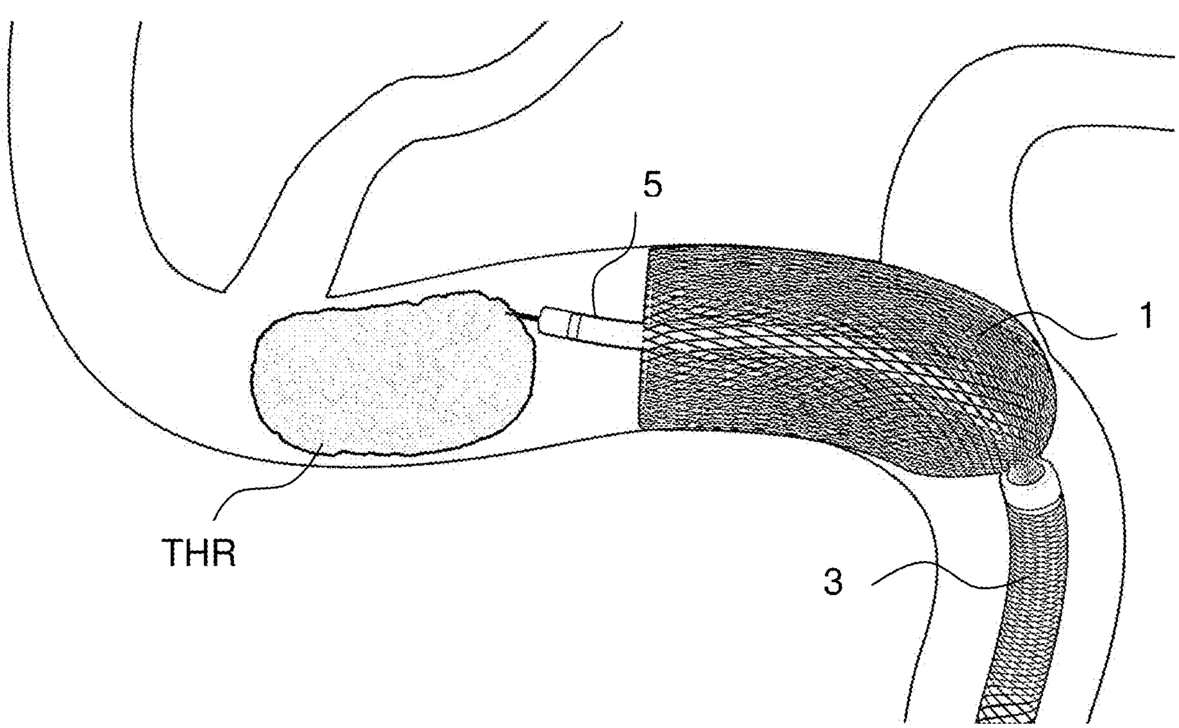
Figure 9:
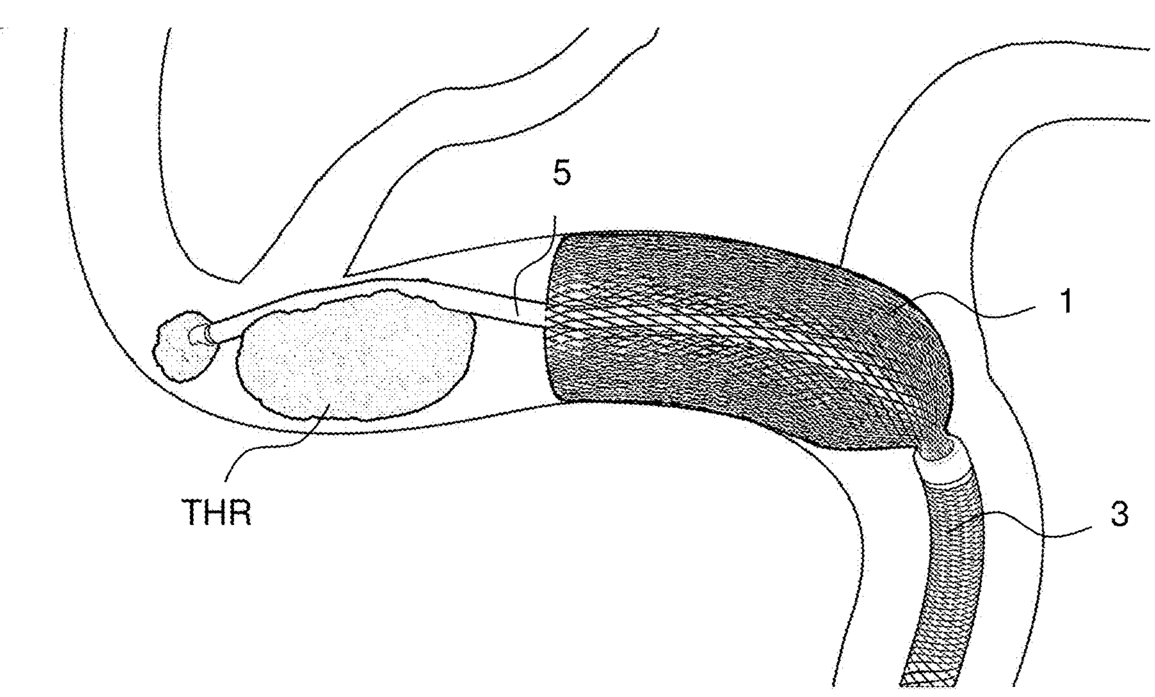
Figure 10:
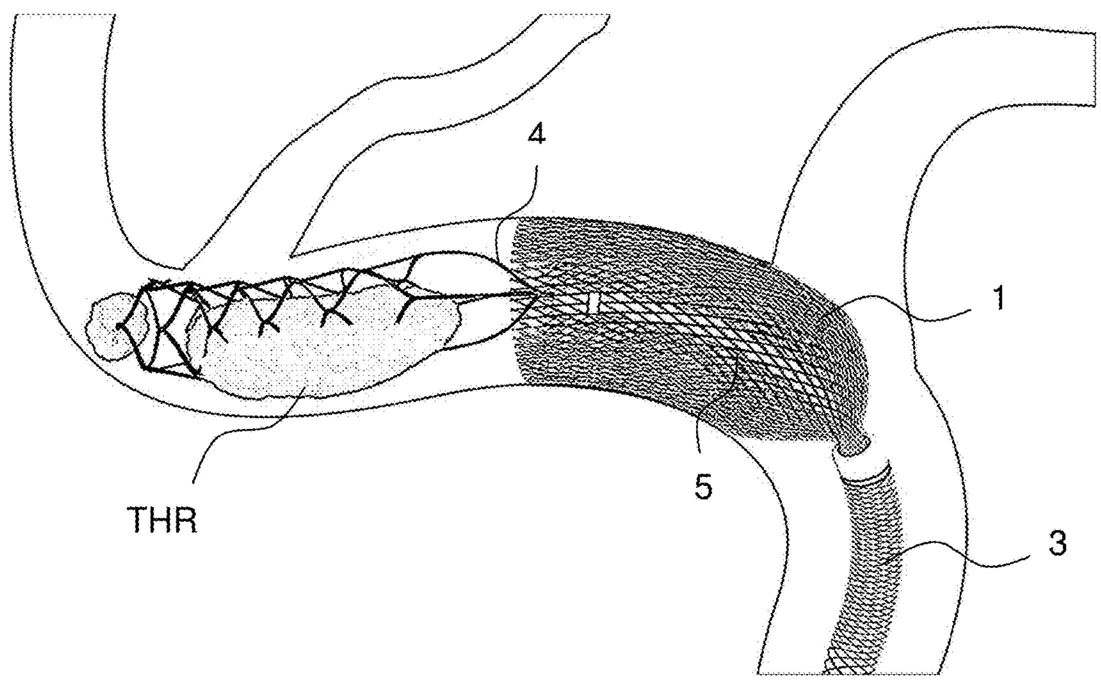
Figure 11:
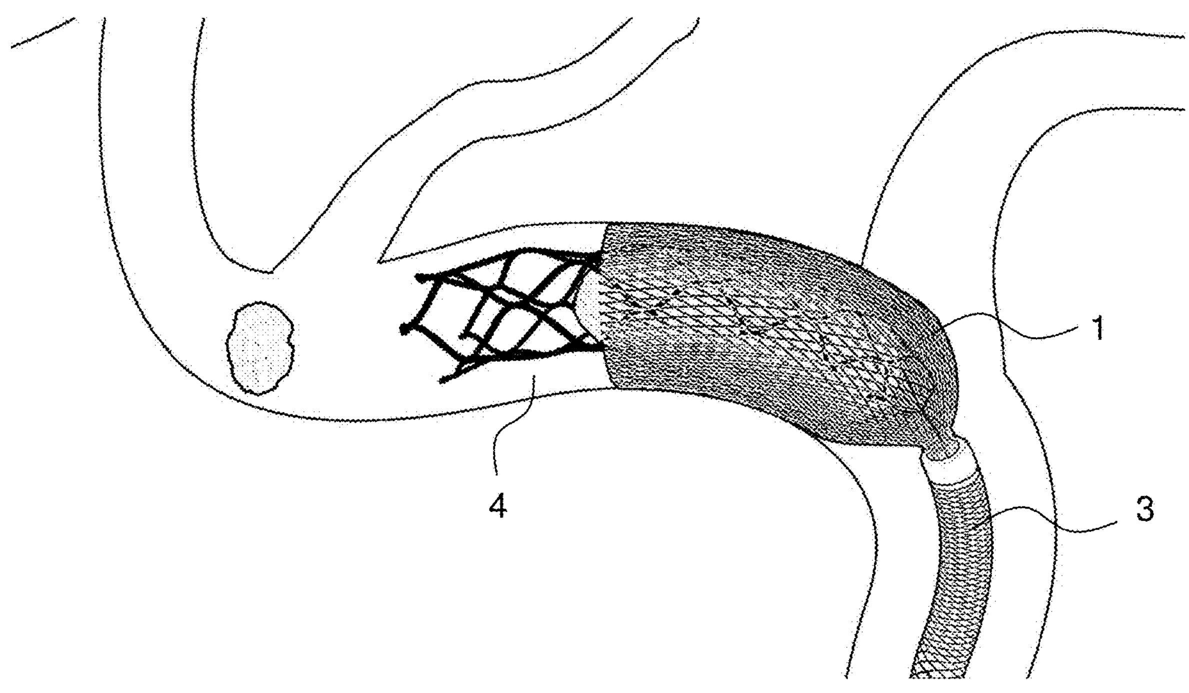
Figure 12:
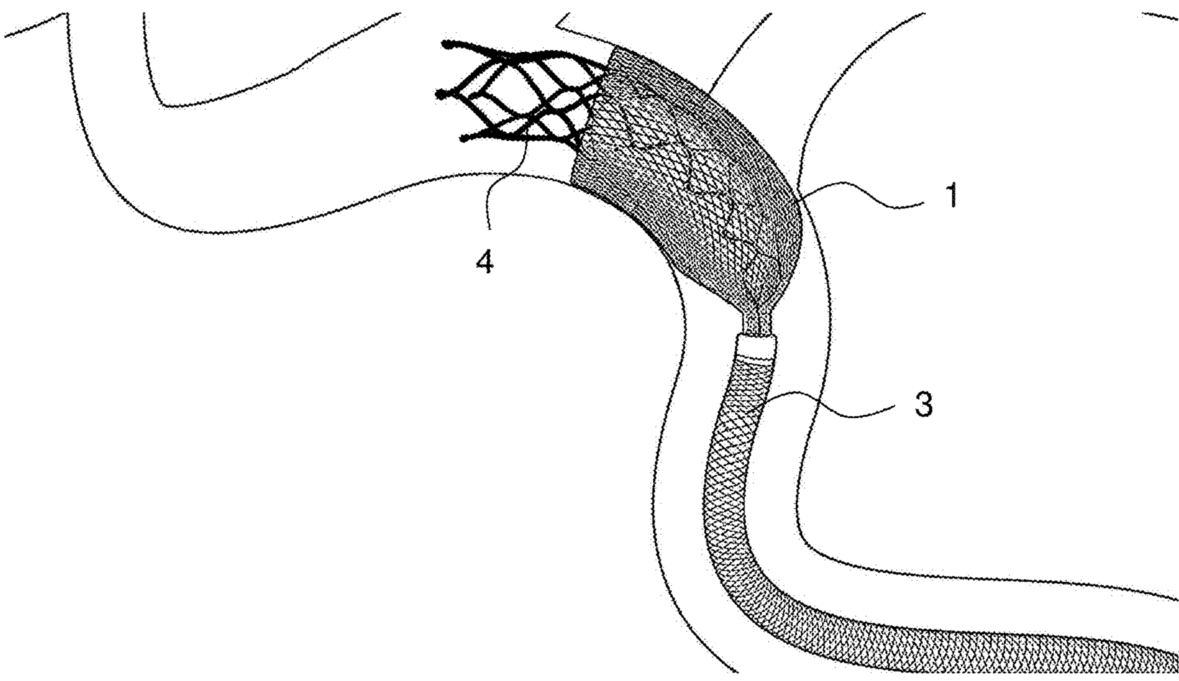
Figure 13:
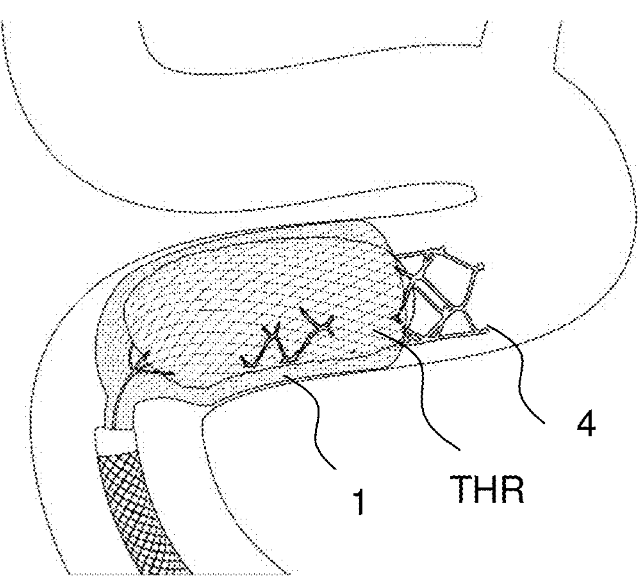
Figure 14:
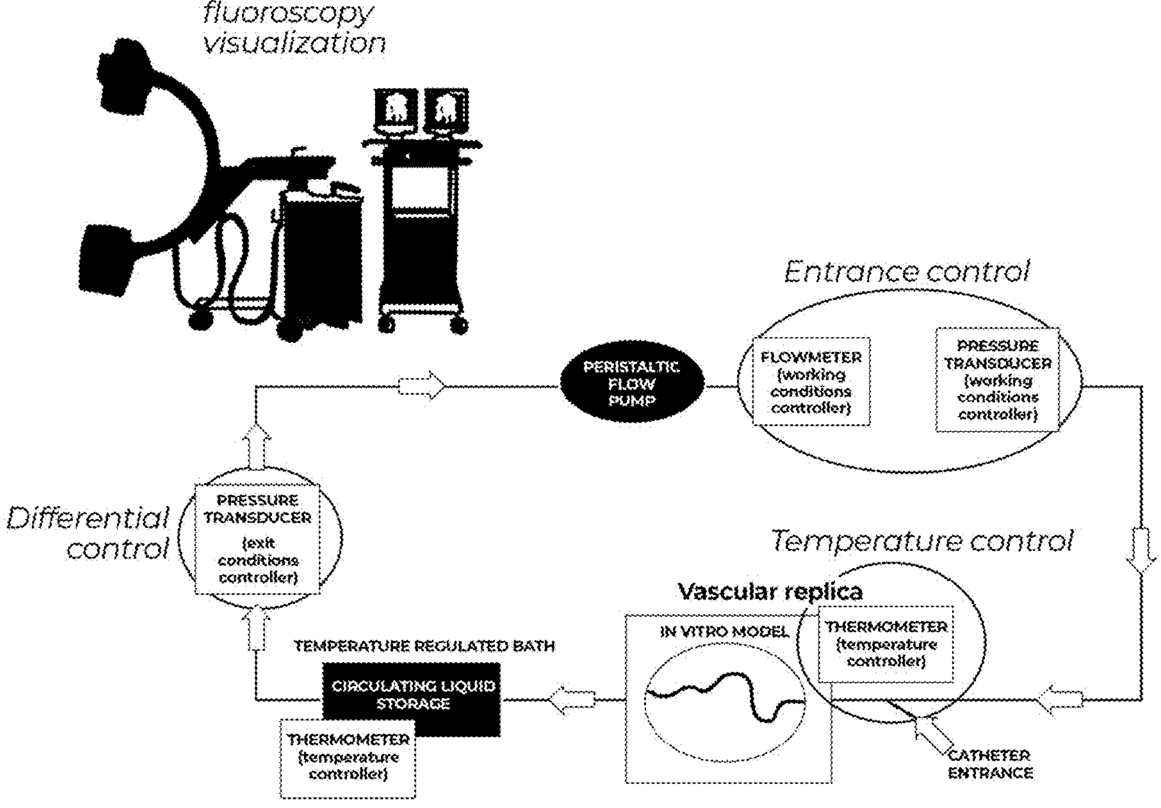
FIG. 14 shows the model system of cerebrovasculature.

FIGS. 6-13 show the steps of a method of extracting a thrombus THR from a thrombus site in a blood vessel of a patient using the ANCD of the invention. Firstly, the delivery catheter 3 containing the expandable-tip aspiration catheter 7 is advanced over a guide wire 6 and the microcatheter 5 to the internal carotid (FIG. 6). Once the delivery catheter 3 reaches its position it is withdrawn to deploy the mouth of the expandable-tip aspiration catheter 7 (FIG. 7-8). The aspiration funnel 1 self-expands to the diameter of the vessel and arterial flow is stopped (i.e. blocked or partially reduced) (FIG. 8). Once the mouth of the aspiration funnel 1 is opened, the microcatheter 5 is advanced into the thrombus THR (FIG. 9). Then the microcatheter 5 is withdrawn to deploy the clot-capture element 4, capturing the clot (FIG. 10). The clot-capture element 4 drags the clot to the aspiration funnel 1 mouth while suction is applied to the aspiration catheter 2 by means of a syringe to aspirate the clot (FIG. 11). Finally, the clot is engaged in the aspiration funnel 1 (FIG. 12) and the system is removed (FIG. 13).

Following some particular experimental examples are detailed. It should be noted that in the following experimental examples, the combination of the delivery catheter 3 and the expandable-tip aspiration catheter will be referred as ANA device. Therefore, the proposed ANCD is comprised of the ANA device, the clot-capture element 4 and the microcatheter 5.

Example 1: In Vitro Assay

1. Study Objectives

This study aimed to assess the performance of the ANA device (i.e. the catheter device comprised of the delivery catheter 3 and the expandable-tip aspiration catheter 7) included in the ANCD. The expandable-tip aspiration catheter 7 was built using a DFT (Nitinol/platinum) braided stent covered with silicone as defined below. The performances were evaluated in an in vitro 3D simulation model, a cerebrovascular model of the intracranial circulation that simulates the carotid and cerebral physiological blood flow, pressure and vessel anatomy including an occlusive ex vivo clot analog.

TABLE 3

| ANA 5.2*9 mm prototype 2018 | | |
|---|---|---|
| Shape parameters | OD sec 20 [mm] | 5.2 |
| | OD sec 32 [mm] | 1.65 |
| | L sec 20 [mm] | 9 |
| | α sec 31 [°] | 31 |
| | L sec 32 [mm] | 3.5 |
| Braiding parameters | Wire OD [μm] | 51 |
| | Wire number | 48 |
| | β sec 20 [°] | 55 |
| | β sec 32 [°] | 45 |

Specifically, this study aimed to assess the efficacy of the ANA device in combination with the clot-capture element 4, such as a stent retriever (SR), in terms of the rate of revascularization and rate of clot embolization.

2. Materials and Methods 2.1 Samples

The ANA devices used in the study were the following (Table 4):

| Funnel Catheter | Funnel Model | Funnel Reference | Delivery Catheter |
|---|---|---|---|
| Group 10/ Sample 8 | 5.2*9 mm | ZA00583-03 | Coiled delivery (new)/ group 10/sample 8 |
| lot 945034 sample 10 | 5.2*9 mm | ZA00599-10 | Coiled delivery (new)/ group 10/sample 8 |
| Sample 2- IVT efficacy | 5.2*9 mm | ZA00600-02 | Sample 3-IVT ANA Compatibility |
| Sample 5 - IVT efficacy | 5.2*9 mm | ZA00600-05 | Sample 3-IVT ANA Compatibility |
| Sample 5 - IVT efficacy | 5.2*9 mm | ZA00601-06 | Sample 3 - IVT efficacy |
| Sample 3-IVT. Efficacy IVT SAB | 5.2*9 mm | ZA00615-03 | Sample 4 - IVT compatibility |
| Group 10/ Sample 8 | 5.2*9 mm | ZA00599-02 | Sample 4 - IVT compatibility |

The marketed devices are shown below (Table 5):

| Device type | | Name | Company |
|---|---|---|---|
| Thrombectomy devices | Stent Retrievers | Solitaire 4- 6 × 20 mm | Medtronic |
| Neurovascular guide catheters | Guide catheter | Neuronmax 088 | Penumbra Inc |
| | Microcatheter | Rebar | Covidien |
| | Distal Access Catheters (DAC) | Navien | Covidien |
| | Balloon Guide Catheter (BGC) | Cello | Covidien |

2.2. Methodology

The study was carried out in the Animal Facility of the Institut de Recerca de Vall d'Hebrón (VHIR), Barcelona (Spain).

Mechanical thrombectomy with the ANA device in combination with stent retrievers (Solitaire), and marketed devices (Solitaire with distal access catheter—"Solumbra-like"—, and Solitaire with balloon guide catheter) was simulated in the model cerebrovascular occlusion (including a clot analog). In addition, the performance of the ANA device, including the navigability and the compatibility with different stent retrievers was also assessed in the presence and absence of clots.

The procedures were followed by low resolution fluoroscopy and assisted by trained technicians.

The model system of cerebrovasculature is composed of a human vascular replica and a physiologically relevant mock circulation flow loop, as described below.

Vascular Replica

A three-dimensional in vitro model of the intracranial circulation was used as vascular replica.

Two models of vascular replica were used:

1. Vascular model Jacobs Institute: This model was designed based on patient vascular anatomy using CT-A imaging (50 patients) and then printed on a 3D printer (Jacobs Institute). The model closely resembles the human intracranial circulation in terms of curvature, diameter, and length, and consists of the internal carotid artery segment and middle cerebral artery branches (M1-M4 segments), bilateral A1 anterior cerebral artery segments connected to a single anterior cerebral artery, and a single posterior communicating artery (right side), thus allowing near complete circle of Willis circulation. In addition, a representative access vasculature compressing the aortic arc and the common carotid artery and cervical internal carotid are also included. The levels of tortuosity of the different sections of the vascular replica are moderate-severe, with an average tortuosity index of 4.752 and 2.332 for the intracranial and the access vasculature, respectively, creating a complete model with a tortuosity index of 7.084.

2. Vascular model UMASS (University of Massachusetts Medical School): A vascular replica of the entire circle of Willis with a severe ICA siphon in terms of curvature, diameter, and length was selected based on data from magnetic resonance angiograms of 20 patients and was built by using a small-batch manufacturing process. An ICA siphon with severe tortuosity is selected to offer challenging tortuosity for endovascular access. During the image post-processing, the 3D reconstruction of the vasculature is modified to rejoin the M2 and A2 divisions resulting in a single output from each vascular territory.

Two vascular replicas with different degree of tortuosity were used:

(1) Moderate vascular model: the different sections of the vascular replica showed an average tortuosity index of 5.831 and 0.047 for the intracranial and the access vasculature, respectively, creating a complete model with a tortuosity index of 5.878

(2) Severe vascular model: the different sections of the vascular replica showed an average tortuosity index of 7.067 and 7.067 for the intracranial and the access vasculature, respectively, creating a complete model with a tortuosity index of 7.233

Mock Circulation Flow Loop

The model was connected to a peristaltic pump. Saline solution heated to 37° C. was circulated through the model using a peristaltic pump. The rate of flow into the full neurovascular model was set at 370-450 mL/min, values based in physiological flow rates. The pressure was also regulated to 180 mmHg, which is in the upper range of clinically representative blood pressure. Flow and pressure sensors were located in the entrance of the circuit, after the peristaltic pump output, while a second pressure sensor placed after the vascular replica calculates the differential pressure. A thermometer measures the fluid temperature in the mid zone. Intravascular devices were maneuvered under fluoroscopic guidance and angiographic images of the vessel were obtained with contrast media to identify the proper location of the target vessel.

2.3. Clot Analogs

For the assessment of the efficacy in clot retrieval (revascularization and embolization rates), soft red and fibrin rich clots were used to generate middle cerebral artery (MCA, M1) occlusions.

Porcine blood clots were fabricated in the VHIR. Soft red and fibrin rich clots were made as per Mokin et al 2016 and Duffy et al 2017, respectively:

Soft red clot: 4 ml of non-anticoagulated porcine blood was mixed with 32 mg of fibrinogen from bovine plasma (F8630, Sigma-Aldrich) and 1 unit of thrombin form bovine plasma (T4648, Sigma-Aldrich) for at least 3 min. The mixture was incubated at room temperature for at least 60 min.

Fibrin rich clot: Porcine blood was anticoagulated using sodium citrate solution (3.2%) immediately after collection. The whole blood constituents were subsequently separated using centrifugation (600 g, 15 min, 4° C.) and the extracted plasma was mixed with the red blood cells (RBCs) in a ratio of 9:1. Coagulation was initiated by the addition of calcium chloride (2.06%) and the clotted material was allowed to mature for 60 min at 37° C. The resultant clots consist of approximately 100% fibrin.

The clot (5×5×7 mm) was injected into the flow loop to form a MCA occlusion. Prior to initiating thrombectomy, complete occlusion with TICI 0 was required.

2.4. Procedure

Neuron Max 088 guide catheter (Penumbra) was placed in the cervical ICA and delivered the guidewire which will be then softly advanced through the target vessel.

Thrombectomy procedure (clot retrieval procedure):

Marketed thrombectomy devices: A microcatheter was navigated over the wire across the occlusive clot. The guidewire was withdrawn followed by deployment of the stent retriever (Solitaire) for mechanical thrombectomy. During retriever retraction, continuous aspiration was applied during retrieval with the assistance of a 60 mL syringe.

ANA in combination with stent retrievers: The ANA was combined with the stent retriever to retrieve the clot: with the stented funnel 1 deployed proximal to the occlusion, the microcatheter 5 with the stent retriever (Solitaire) in it was navigated through the aspiration catheter 2 and the deployed stented funnel 1 over the wire until reaching and crossing the clot. The stent retriever was deployed to capture the clot while continuous aspiration was applied via ANA, the stent retriever was dragged until the whole clot was safely placed inside the stented funnel 1 and both devices were finally retrieved as a whole. In specific procedures aspiration was not applied.

2.5. Evaluation Methodology (1) Assessment of the Efficacy:

REVASCULARIZATION: Flow was evaluated following the procedure time points after all procedure execution. TICI 2b and 3 are considered successful revascularization (1). TICI 0, 1, and 2a are considered unsuccessful revascularization (0). Time points:

Pre-clot placement (for baseline of model vasculature)
Pre-treatment (baseline of ischemia, clinical starting point)
Post-thrombectomy pass 1 (“first pass revascularization”)
Post-thrombectomy pass 2 (if appropriate)
Post-thrombectomy pass 3 (if appropriate)

The main endpoints considered in the efficacy assessment were:

Rate of revascularization after first pass (TICI 2b-3)
Rate of revascularization after 3 passes (TICI 2b-3)

EMBOLIC EVENTS (ENT/EDT). Flow was evaluated following the procedure time points after all procedure execution. Distal Territory (EDT) and Emboli New Territory (ENT) are assessed. EDT score of 0 and ENT score of 0 is indicative of no embolic events. EDT score of 1 and ENT score of 1 is indicative of an embolic event. Time points:

Pre-clot placement (for baseline of model vasculature)
Pre-treatment (baseline of ischemia, clinical starting point)
Post-thrombectomy pass 1 (“first pass revascularization”)
Post-thrombectomy pass 2 (if appropriate)
Post-thrombectomy pass 3 (if appropriate)

The endpoints considered in the efficacy assessment were:

EDT and ENT after first pass (TICI 2b-3)
EDT and ENT after 3 passes (TICI 2b-3)

(2) Assessment of Navigability:

Navigability was assessed after the first attempt. The following endpoints were used to assess navigability:

Navigation time [s]: the time required to reach the target vessel
Navigability/flexibility: ratio between the navigation time and the score “Pushability of the device to the target vessel. Proximal control of the device”

2.6. Experimental Design

Table 6 shows the experiments that were carried out for each group and each condition for different assessments. The maximum number of thrombectomy attempts (passes) was limited to 3.

TABLE 6

Experimental design

EFFICACY OF MARKET DEVICES ENDPOINTS

| revascularization 1$^{st}$ pass | revascularization 3$^{rd}$ pass | Distal embolization (EDT) | New territory embolization (EDT) |
|---|---|---|---|

| DEVICES | SAMPLE SIZE | VASCULAR MODEL | CLOT type | CLOT location |
|---|---|---|---|---|
| Solitaire + BGC | 10 | Jacobs | Soft red | MCA-M1 |
| | 10 | Jacobs | Fibrin rich | MCA-M1 |
| | 5 | UMASS moderate | Soft red | MCA-M1 |
| | 5 | UMASS moderate | Fibrin rich | MCA-M1 |
| | 5 | UMASS severe | Soft red | MCA-M1 |
| | 5 | UMASS severe | Fibrin rich | MCA-M1 |
| Solitaire + DAC | 5 | Jacobs | Soft red | MCA-M1 |
| | 5 | Jacobs | Fibrin rich | MCA-M1 |
| | 5 | UMASS moderate | Soft red | MCA-M1 |
| | 5 | UMASS moderate | Fibrin rich | MCA-M1 |
| | 5 | UMASS severe | Soft red | MCA-M1 |
| | 5 | UMASS severe | Fibrin rich | MCA-M1 |

TABLE 6-continued

| Experimental design | | | |
|---|---|---|---|
| EFFICACY OF ANA COMBINED WITH STENT RETRIEVERS ENDPOINTS | | | |
| revascularization 1$^{st}$ pass | revascularization 3$^{rd}$ pass | Distal embolization (EDT) | New territory embolization (EDT) |

| DEVICES | SAMPLE SIZE | VASCULAR MODEL | CLOT type | CLOT location |
|---|---|---|---|---|
| ANA + Solitaire | 7 | Jacobs | Soft red | MCA-M1 |
| | 7 | Jacobs | Fibrin rich | MCA-M1 |
| | 5 | UMASS moderate | Soft red | MCA-M1 |
| | 5 | UMASS moderate | Fibrin rich | MCA-M1 |

| DEVICES | ASPIRATION | SAMPLE SIZE | VASCULAR MODEL | CLOT type | CLOT location |
|---|---|---|---|---|---|
| ANA + stent retriever | YES | 17 | Jacobs | Soft red | MCA-M1 |
| | | 16 | Jacobs | Fibrin rich | MCA-M1 |
| | | 5 | UMASS moderate | Soft red | MCA-M1 |
| | | 5 | UMASS moderate | Fibrin rich | MCA-M1 |

2.8. Data Analysis

Revascularization and embolization values were expressed as percentage; the mean per group was calculated.

Performance scores were qualitatively analyzed. Mean and SD per group were also calculated.

Integrity data was assessed qualitatively.

Statistical analyses of revascularization, embolization and navigability values were conducted with Excel. T-test was applied to compare means of two groups, a value of $p \leq 0.05$ was considered statistically significant.

3. Results (Expressed in %)

TABLE 7

(intrac = intracerebral):

| Cerebrovascular models | | | | | ANA + Solitaire | | | BGC + Solitaire | | | DAC + Solitaire | | |
|---|---|---|---|---|---|---|---|---|---|---|---|---|---|
| Model | | tortuosity Index (TI) | Global TI | Clot type | n | 1st pass | 3rd pass | n | 1st pass | 3rd pass | n | 1st pass | 3rd pass |
| Jacobs | access | 2.33 | 7.08 | soft red | 10 | 100 | 100 | 10 | 100 | 100 | 10 | 80 | 90 |
| Tortuous access | intrac | 4.75 | | fibrin rich | 15 | 87 | 100 | 14 | 29 | 29 | 13 | 77 | 85 |
| UMASS | access | 0.05 | 5.88 | soft red | 10 | 100 | 100 | 10 | 80 | 80 | 10 | 90 | 100 |
| Moderate tortuosity | intrac | 5.83 | | fibrin rich | 15 | 93 | 100 | 15 | 67 | 93 | 16 | 75 | 88 |
| UMASS | access | 0.17 | 7.23 | soft red | 5 | 100 | 100 | 5 | 100 | 100 | 5 | 100 | 100 |
| Severe Tortousity | intrac | 7.07 | | fibrin rich | 5 | 100 | 100 | 5 | 60 | 80 | 6 | 100 | 100 |

Figure 15:
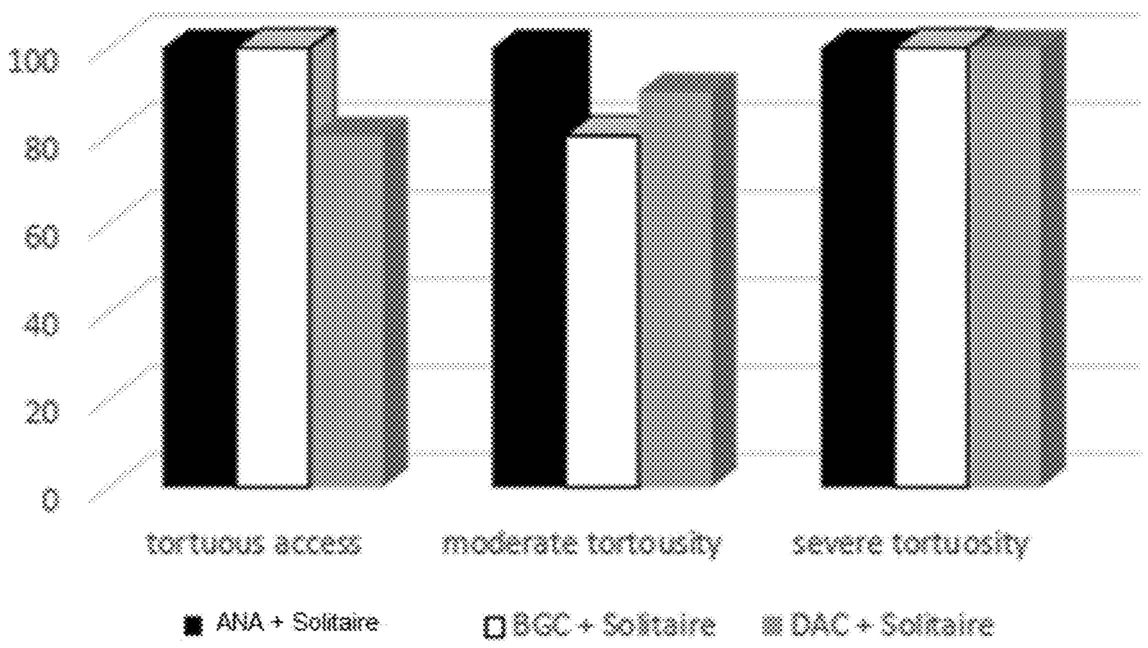
FIG. 15 shows the rate of revascularization after a single pass in different models using soft red clots.
Figure 16:
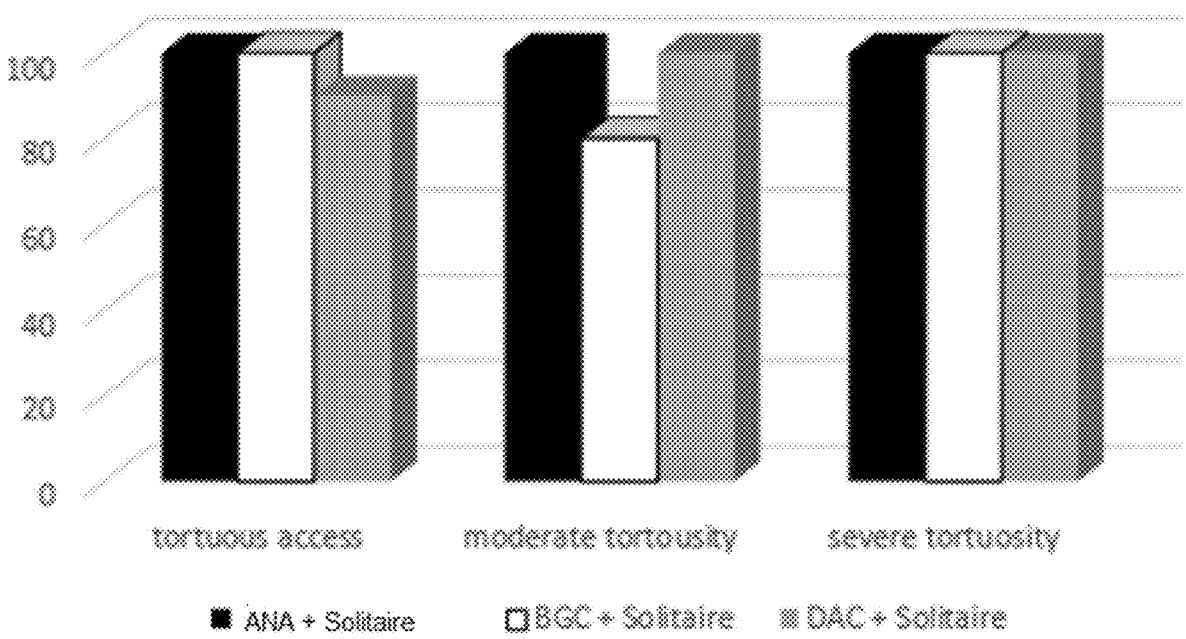
FIG. 16 shows the rate of revascularization after the third pass in different models using soft red clots.

With soft red clots the results of combining ANA with Solitaire were better or equal than combining Solitaire with a Balloon Guiding Catheter (BGC) or a Distal Access Catheter (DAC) (FIG. 15). Similar results were observed at the first pass and at the third pass in all three models (FIG. 16).

Figure 17:
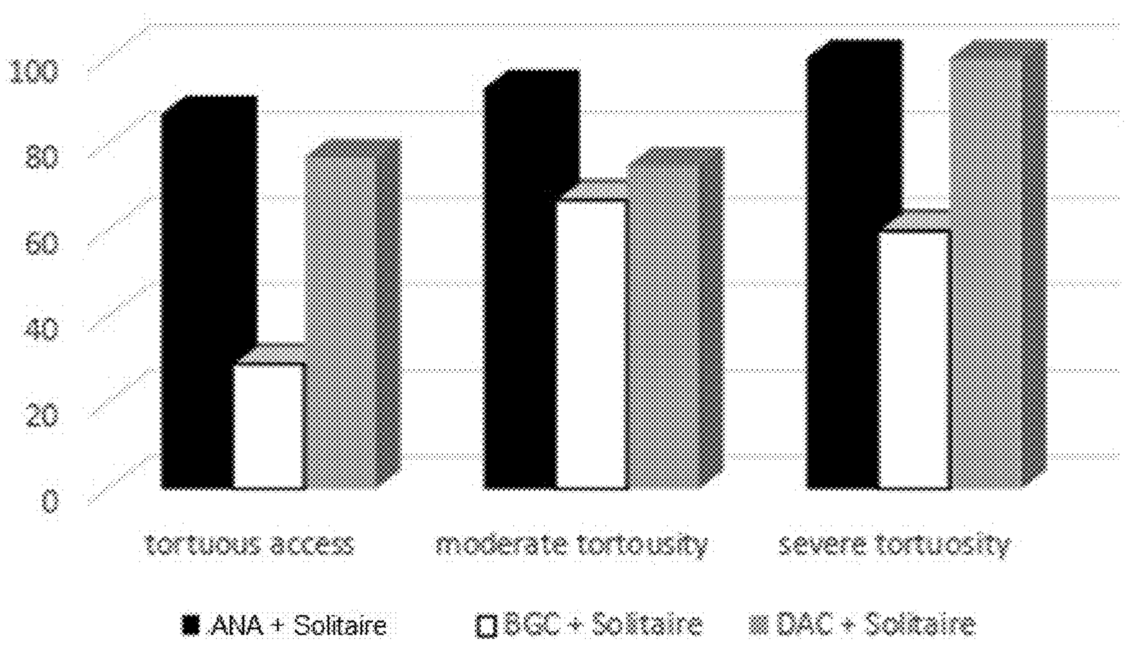
FIG. 17 shows the rate of revascularization after a single pass in different models using fibrin rich clots.
Figure 18:
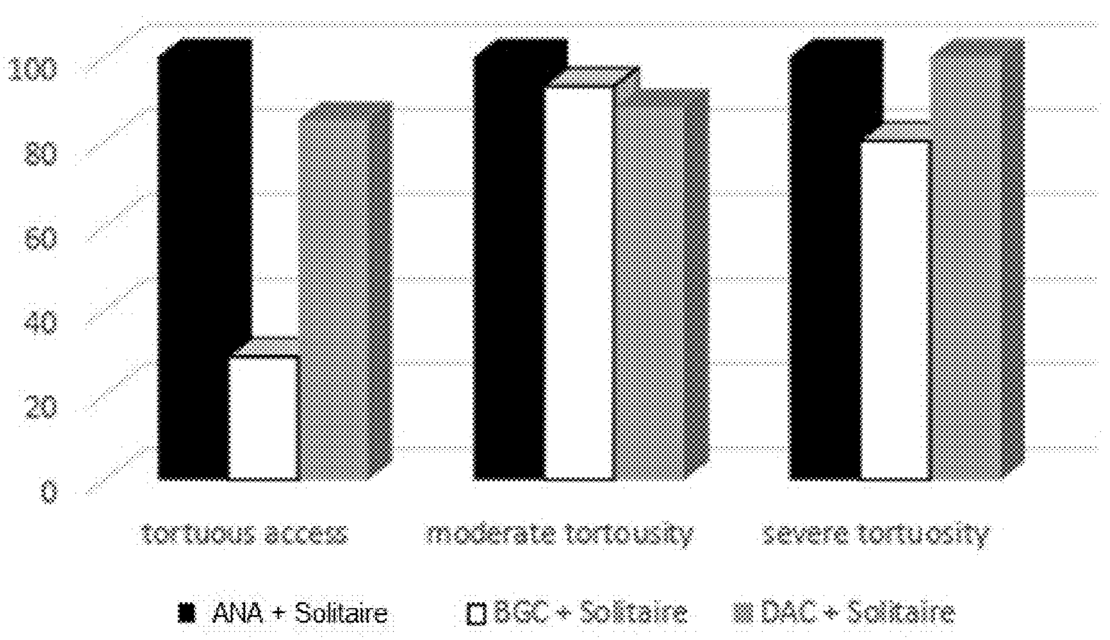
FIG. 18 shows the rate of revascularization after the third pass in different models using fibrin rich clots.

With fibrin rich clots the results of combining ANA with Solitaire were always better than combining Solitaire with a Balloon Guiding Catheter (BGC) or a Distal Access Catheter (DAC) (FIG. 17). Similar results were observed at the first pass and at the third pass in all three models (FIG. 18).

With the other stent retrievers similar results were observed (data not shown).

4. Conclusions

ANA in combination with stent-retriever showed significantly better recanalization rates in a smaller number of passes as compared to other commonly used device combinations such as BGC or DAC in combination with stent retriever especially with fibrin rich clots.

Extrapolating these results to the clinical practice, it would be better to treat Acute Ischemic Stroke on large vessel occlusion and clinical mismatch directly with ANA combined with a stent Retriever. This combination would avoid the need to use a rescue therapy.

Example 2: In Vivo Assay: Chronic Evaluation of Performance and Safety of the ANA in Combination with a Clot-Capture Element (for Example a Stent Retriever (SR)) in a Swine Clot Model 1. Introduction and Objectives Endovascular treatment (EVT) is recognized as the most effective treatment for large vessel occlusion (LVO) strokes.

Highest degree of recanalization in the shortest time with the minimum number of attempts has been demonstrated to correlate with improved clinical outcomes. Although highly effective, failure to reach complete recanalization has been reported in about 20% of treated patients. In order to improve patient outcomes, different devices and combinations are under development to increase the first pass complete recanalization rate. The development of such devices includes preclinical testing in phantom models simulating the cerebrovascular human anatomy, and animal models in which device related vessel injury can be assessed. Each simulation model has its own characteristics and therefore it is recommended that any new device or combination will prove its efficacy and safety in different conditions before final evaluation in a first in human study.

The aim of this study was to evaluate the pre-clinical efficacy and safety of the ANCD, in conjunction with adjunct devices, in a swine model 3 and 30 days following 3 passes, and specifically confirm that the use of the self-expanding funnel 1 is unrelated to higher vascular injury in comparison with commonly used devices. The study design was as follows:

Acute performance evaluation on day 0 with regards to the efficacy in vessel revascularization (clot retrieval).

Angiographic and histological evaluation after 3 and 30 days to evaluate local and end organ tissue response.

2. Methods

The ANA device in this case includes the delivery catheter 3 and the expandable-tip aspiration catheter 7.

The expandable-tip aspiration catheter 7 is comprised of highly flexible polymers onto a braided metallic structure. It is intended to restrict locally the blood flow during the intervention. It includes the self-expanding funnel 1 that, when unsheathed, can expand to the diameter of the blood vessel, adapting to its shape, thereby restricting the blood flow. The expandable-tip aspiration catheter 7 can provide an effective aspiration that serves as a complementary mechanism when combined with retrieval devices. The aspiration funnel 1 is designed to have enough flexibility to adapt to the neurovascular tortuosity. The aspiration funnel 1 is comprised of a radiopaque braid and a polymeric film.

The delivery catheter 3 is the outermost catheter of the ANA device, which navigates until reaching the target vessel. It has a hydrophilic coating to reduce friction during use and a radiopaque marker on the distal end for angiographic visualization. The materials used allow enhanced flexibility in the tip and sufficient stiffness and pushability of the proximal portion.

Animal Model

All animals were held in quarantine and housed at CBSET (Lexington, Mass., USA), where the study was conducted, a facility accredited by the American Association for Accreditation of Laboratory Animal Care, under conditions that met or exceeded requirements as set forth in the USDA guidelines. Standard veterinary practices were performed during quarantine, including physical examinations and clinical pathology to determine health status before assignment to the study. A nutritionally balanced diet appropriate for the species was offered daily to all animals with water ad libitum.

Eleven pigs were used in this study (female or castrated male Yorkshire pigs, weight 39-50 Kg). The swine model was chosen as the experimental species for this study because the size and anatomy of the vascular system is clinically relevant for the purpose of testing catheter-based medical devices for the treatment of vascular disease. Also, swine is an established animal model for vascular studies and generally accepted as a scientific standard.

Animals were anesthetized, intubated, and IV catheterized for the administration of supportive IV fluids and medications. The surgical procedures were performed under aseptic conditions. Physiological parameters were monitored through all the procedures. The femoral artery was accessed via cutdown approach. A 9 F introducer sheath was advanced into the artery and heparin (150 U/kg, IV) was administered to prolong Activated Clotting Time (ACT) to approximately 200-350 seconds. ACT levels were monitored every 45 minutes during all the procedures, and additional heparin was administered as needed to maintain the target ACT. Under fluoroscopic guidance, an 8F Mach 1™ guide catheter (CGC: Boston Scientific, Marlborough, MA) was advanced through the sheath over a guide wire into the descending aorta and to the target arteries. Angiographic images of the vessels were obtained with contrast media to identify a suitable location for the treatment site. Angiograms were performed throughout the procedure: baseline, after each pass, and prior to necropsy. The parameters assessed by angiography (qualitative and quantitative) were the following: vessel anatomy, target site, device monitoring, vessel status-injury, vasospasm, and blood flow (mTICI scale).

Two different recanalization strategies were tested per Instructions for Use (IFU) for the interventions of the target vessels:

1—BGC+SR: Balloon Guide Catheter (BGC: 8Fr FlowGate2™ Balloon Guide Catheter (95 cm); from Stryker Neurovascular, Fremont, CA)+stent retriever (SR: Solitaire™ 2 4×40 mm; Medtronic Neurovascular), and

2—ANA+SR.

Cervical and lingual arteries were targeted. These arteries cover the diameter range between 2.2 and 5 mm for ANA and SR, and 2.7 to 5 mm for the BGC, which represents the size of the target vessels in the cerebrovasculature (internal carotid artery (ICA), middle cerebral artery (MCA)).

ANA+SR and BGC+SR devices were distributed among target vessels to ensure that assessment was made in all vascular beds at each time point. Randomization of animals was not required for this study as each animal had both ANA+SR and BGC+SR devices evaluations.

In order to study the devices in a clinical simulation as a worse case, three passes in every study group were assessed in all cases (the maximum number of deployments and retractions allowable for the ANA device and the Solitaire stent retriever as per IFU). The potential vascular injury caused by the devices (perforation, dissection, thrombosis) and vasospasm was also assessed during the procedure by angiography.

Clots Preparation and Delivery

Firm (high fibrin) and soft clots, previously generated with autologous blood (24-48 h) were administered in target treatment vessels: cervical and lingual arteries. Vessels and clot consistency were randomly selected to ensure even distribution of test and control devices. Firm clots were prepared using whole blood samples (50 mL) collected into standard tubes, centrifuged and extracting the serum layer plus 10% of the lower red blood cell layer including the buffy layer. This extracted solution was mixed and incubated for two hours. Swine blood (up to 30 mL), was incubated at room temperature for two hours for generating the soft clots. In both cases the solid component was stored at 4° C. in contrast filled containers until the time of the procedure. Clots were cut to a size appropriate for the target vessel prior to administration. Clots were introduced to the target region through the 8F guide catheter via a customized luer to minimize shear/fragmentation. A follow up angiography was done to confirm vessel occlusion (TICI 0). Clots were allowed to stabilize in the vessel prior to treatment for 5-10 minutes before thrombectomy.

Thrombectomy Procedures

Mechanical thrombectomy procedure was performed with the ANA device or BGC in combination with the SR for the assessment of the ability to retrieve clot. TICI flow (mTICI scale) and vasospasm was assessed following clot administration and after each thrombectomy attempt.

Intravascular devices were maneuvered under fluoroscopic guidance and angiographic images of the vessels were obtained to identify the proper location of the device.

In all interventions, a microcatheter 5 (Rebar 18, Medtronic Neurovascular) was advanced over a 0.014" micro guidewire (Synchro; Stryker) to the proximal aspect of the occluding clot. In intervention 1, the BGC was inflated to arrest flow before thrombectomy was performed with the SR, as per IFU and usual practice; aspiration was applied through the BGC while the SR was pulled out, with the microcatheter 5 in place. In intervention 2, the delivery catheter 3 was advanced close to the proximal aspect of the clot and the aspiration funnel 1 deployed proximal to the clot creating local flow arrest. The microcatheter 5 was then advanced through the clot and the SR deployed as in usual practice. At this point the microcatheter 5 was completely withdrawn to increase aspiration force through the expandable-tip aspiration catheter 7. The SR was then slowly pulled until its proximal end was inside the aspiration funnel 1, aspiration was initiated, and the ANA+SR were progressively conjunctively pulled out.

In all interventions, aspiration during the thrombectomy procedure was performed with a 60 cc syringe (Vaclock; Merit Medical) connected to a three-way stopcock through either the BGC (intervention 1), or the expandable-tip aspiration catheter 7 (intervention 2). For each clot, recanalization attempts with the same strategy were repeated in 2 more passes (last pass). An angiogram was performed after each pass to assess recanalization (TICI flow) and vasospasm. The recanalization rates (TICI 3) were calculated considering the first and third pass TICI data.

The resulting study design is summarized in the following Table 8:

TABLE 8

Study design: Testing devices (ANA, FlowGate BGC and Solitaire), number and location of vessels, number of animals involved and time point assessments.

| Test/ Control Device | Number of Vessels/ Treatment Scheme | | Number of Animals | Time Point |
|---|---|---|---|---|
| ANA + Solitaire | Cervical or lingual arteries, soft clot n = 3<br>Cervical or lingual arteries, firm clot n = 3 | n = 6 | 5 | Day 3 |
| FlowGate BGC + Solitaire | Cervical or lingual arteries, soft clot n = 3<br>Cervical or lingual arteries, firm clot n = 3 | n = 6 | | |
| ANA + Solitaire | Cervical or lingual arteries, soft clot n = 3<br>Cervical or lingual arteries, firm clot n = 4 | n = 7 | 6 | Day 30 ± 2 |
| FlowGate BGC + Solitaire | Cervical or lingual arteries, soft clot n = 4<br>Cervical or lingual arteries, firm clot n = 3 | n = 7 | | |

Histopathology

Animals were euthanatized after 3 and 30 days and underwent a comprehensive necropsy. Treated vessels were dissected and relevant tissues/organs were collected, fixed in 10% NBF (Neutral Buffered Formalin) and paraffin embedded and stained with H&E (hematoxylin and eosin) and Verhoeff's for histomorphologic assessment. Each treated vessel was trimmed to yield at least six cross-sections (2 proximal, 2 mid and 2 distal) within the putative area of treatment. The proximal and mid sections were within the deployment site of the test or control device, the distal section was taken within the clot/stent retriever (Solitaire) region. For lingual treatments, the treated vessel sections were taken from the breadloafed tongue sections and may include surrounding parenchyma. Additionally, untreated distal sections of the vessel were obtained within approximately 5 mm of the distal end of the putative treated area.

Light microscopy was used to determine histomorphological scoring of parameters that reflected the degree and extent of the host response/repair process to the treatment in target vessels. Histomorphometric markers included: vascular injury, vascular mural compression lesion, inflammation, endothelization, luminal fibrin/thrombus deposition, neointima formation, and adventitial fibrosis. Histologic sections of vessels were also examined for other microscopic changes including hemorrhage, necrosis, and type and relative amounts of inflammatory cell infiltrates. Sections of representative downstream tissues were evaluated for any adverse effects associated with treatment, including thrombosis, necrosis, inflammation and presence of embolic material. Scoring values were calculated for every section and level and reported as an overall mean of each vessel, ranking from 0 (no injury) to 3 (highest possible degree of injury) in all markers except for endothelization than ranked from 0 (absence of endothelial covering) to 4 (complete endothelial covering). The pathologist was blinded to the treatment matrix at the time of the pathologist read.

Statistical Analysis

Frequency statistical analysis was obtained, and comparisons were made using the SPSS 17.0 statistical package (SPSS, Inc.). Statistical significance for intergroup differences was assessed by the Pearson $\chi 2$ or the Fisher exact test for categorical variables and the Student's t-test and analysis of variance for continuous variables. When indicated, Mann- Whitney U- and Spearman tests were used. A probability value of <0.05 was considered significant for all tests.

3. Results

Angiographic Results

A total of 26 thrombectomy interventions were performed in 11 animals (BGC+SR: 13 interventions, ANA+SR: 13 interventions).

The results of the study using the ANA device and the FlowGate BGC, both in conjunction with a Solitaire device are shown in Table 9, where the revascularization rates after the first and third passes with soft and firm clots are shown.

TABLE 9

Recanalization rates at first and third passes using ANA + SR and BGC + SR.

| | In vivo model | | | | | |
|---|---|---|---|---|---|---|
| | ANA + SR | | | BGC + SR | | |
| clot type | n | 1st pass | 3rd pass | n | 1st pass | 3rd pass |
| soft clot | 6 | 67% | 100% | 7 | 29% | 86% |
| firm clot | 7 | 71% | 100% | 6 | 67% | 67% |
| total | 13 | 69% | 100% | 13 | 46% | 77% |

With soft clots the results of combining ANA with Solitaire were always better than combining Solitaire with a Balloon Guiding Catheter (BGC), in both, first and third passes.

With firm clots the results of combining ANA with Solitaire were always better than combining Solitaire with a Balloon Guiding Catheter (BGC), in both, first and third passes.

After 1st pass, recanalization rates (TICI 3) were ANA+SR: 69% and BGC+SR: 46%. With additional passes, recanalization rates increased in both treatment groups: ANA+SR: 100% vs BGC+SR: 77%. The mean number of passes to achieve complete recanalization tended to be lower with ANA+SR (1.4) as compared to BGC+SR (1.9).

The ANA device performed similarly to the FlowGate control with respect to compatibility between device components and ancillary devices, pushability of the catheter through the anatomy, radiopacity of the catheter, and device integrity after use. The ANA was slightly better in regard to navigating/tracking through the vessel and flexibility, compared to the FlowGate BGC.

One distal embolization was observed by angiography and confirmed at 3-day in the BGC+SR group, while no distal thromboembolic events were observed in ANA+SR group.

The angiography showed that three dissections occurred during the interventions: one in the ANA+SR group and two in the BGC+SR group, none of them were related to the ANA or Solitaire devices as they were immediately observed after catheterization of the target arteries either with the guiding catheter or the BGC. The second dissection in BGC+SR group was mild and not associated with further complications.

As for occlusions, a total of seven were observed after 3 or 30 days. Two detected after 30 days (one for ANA+SR and one for BGC+SR), were subsequent to severe dissections. Three (one for ANA+SR after 3 days, and two for BGC+SR after 3 and 30 days, respectively), were considered inherent procedural complications. The last two occlusions observed at 3 days angiography (two for BGC+SR) were related to the failure to retrieve the clot after at the end of the procedure (up to three passes). No vessel perforation was observed in either group. Vasospasm was a common observation to varying degrees in both groups. This is a common observation in the swine model as pigs are prone to vasospasm.

Histological Results

A total of 24 vessels (2 of the 26 vessels were discarded due to severe dissections) and related downstream tissues were histologically assessed. Histomorphologic markers of vascular mural injury were absent to minimal and were comparable in ANA+SR and BGC+SR groups at 3 days and 30 days. In general, all markers including vascular injury, vascular mural compression inflammation, thrombus, or haemorrhage, and others, were absent to minimal, showing scores below or around 1 in both groups and time points. Endothelial coverage was lowest at the 3 days (ANA+SR: 1.78±1.22, BGC+SR: 2.03±1.20; p=NS), and increased over time to be nearly fully circumferential by day 30 across both groups (ANA+SR: 3.77±0.23, BGC+SR: 3.50±1.07; p=NS).

Thus, vessel injury was absent to minimal, and comparable for both ANA+SR and BGC+SR groups at 3 days and 30 days, as not statistically differences were found. Other findings of inflammation, thrombosis, embolization and necrosis in downstream tissues to cervical artery (brachiocephalicus muscle) and lingual artery (tongue) were also absent to minimal in both groups and time points, with most scores 0 and below 1.

4. Conclusions

The present study in a swine clot model, shows that the ANA device in combination with the Solitaire™ 2 has a safety profile comparable to balloon guide catheter combined with the same stent retriever. Moreover, the observed efficacy profile parallels the finding achieved in previous preclinical studies using in 3D printed phantoms (Example 1), despite differences in vessel tortuosity and experimental environment.

The findings in the histopathological analysis confirm that the ANA device does not exert a deleterious impact on arterial walls with minimal findings comparable with the BGC+SR group. In order to characterize the safety profile in situations mimicking real human cases, target arteries were selected to have 2.2-5 mm. These diameters are smaller than arterial segments where guide catheters and BGC are usually placed. This may be the reason of the few arterial dissections and occlusions that were observed secondary to guiding catheter/BGC manipulations previous to ANA/SR deployment.

The innovative design of the aspiration funnel 1, a self-expandable braided component that adapts to the vessel, fitting to the wall, that combines with the aspiration and consequent local vacuum, intuitively would suggest the risk of significant vessel damage, greater than conventional intravascular devices used in routine neurothrombectomy. But according to the present results, the design of the aspiration funnel 1 and the entire ANA device is atraumatic to the vasculature, mainly due to the balanced radial force of the aspiration funnel 1, sufficient to adapt to the vessel and allow aspiration, but not excessively high to damage the vessel wall, together with the smooth silicone covering of the aspiration funnel 1. Additionally, the catheters surface and tip are smooth with lubricious coating to facilitate the navigation and avoid the vessel trauma. The favorable safety profile in treated vessels is demonstrated by the histopathological and angiography assessment which clearly show that the vessel injury caused by the ANA device combined with the SR is not relevant and similar to the BGC+SR, as histomorphological markets scores are absent to minimal, no perforations occurred, while the cases of dissections were unrelated to the ANA device and associated to the procedure (BGC or guide catheter).

Remarkably, the ANA device in combination with the stent retriever achieved high rates of complete recanalization in a low number of passes; thus, the proposed ANCD presents an improved efficacy profile than the current commercial product. The observed efficacy rates are in line with the recanalization rates achieved in Example 1 (in vitro model). Moreover, the fact that the BGC+SR combination showed similar recanalization results in both models and in real patients may indicate that the results of human clinical studies with ANCD will be in line with the present results obtained in preclinical models.

Recent publications have pointed that not only a higher degree of recanalization is associated with better outcome but also that achieving the same recanalization degree in fewer passes, ideally in a single pass, is also a predictor of improved long-term outcome. These publications also point that currently approved and widely used thrombectomy devices and combinations are capable of achieving first-pass complete recanalization rates ranging 40-50%. Novel devices such as the proposed ANCD, with improved efficacy profiles able to increase the first and final pass success rate will probably lead to improved short and long-term outcome in stroke patients undergoing EVT.

The ANA device, and consequently the ANCD, is designed to induce local flow arrest in combination with a complete clot ingestion into the aspiration funnel 1 that prevents fragmentation and distal embolization. These features are supported by the preclinical observations in both phantom printed in vitro model (Example 1) and this animal study using soft and firm clots. These encouraging results could not be used as predictors of similar success rates in the first in human studies but likely represent the best preclinical evidence that can be achieved at this stage. Moreover, the results observed in this study show an ANA+SR safety profile similar to the commonly used BGC+SR combination.

The reported study was performed under Good Laboratory Practice in an independent facility and the results were directly obtained from the official regulatory report.

Conclusions can be summarized as follows:

1. Pre-clinical results in the swine clot model supports the high efficacy of the ANA+SR without causing clinically significant vessel injury potentially related to the novel funnel component.

Figure 19:
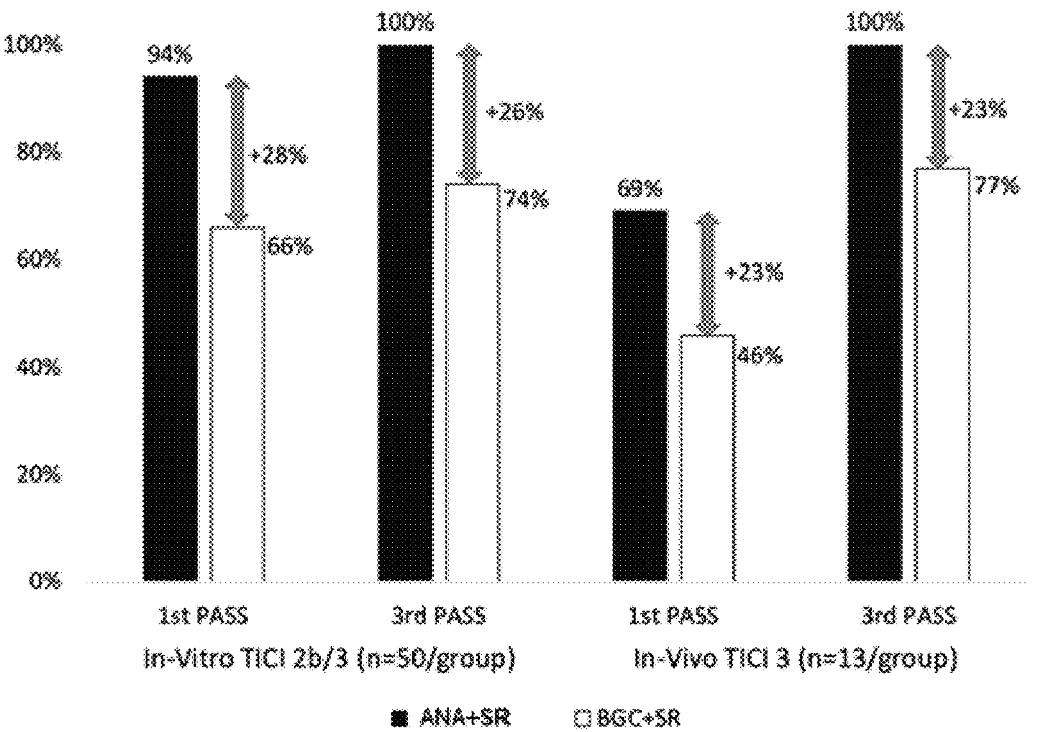
FIG. 19 shows a comparison of recanalization rates after 1st pass and 3rd pass in the combination of the ANA+SR and the BGC+SR groups of in the in vitro study (Example 1, with a sample size of 50) and the in vivo study (Example 2). The absolute increase in recanalization rate with ANA+SR as compared with BGC+SR was similar in both study models.

2. The efficacy profile in this in vivo study was similar to in vitro phantom models (Example 1, FIG. 19), reinforcing the ANA device is highly effective in mechanical thrombectomy when combined with stent retrievers maintaining a similar safety profile than commonly used devices.

3. This study demonstrated that the ANCD performed better than the FlowGate™ Balloon Guide Catheter with respect to handling, positioning, and pushability and trackability.

4. There were no health or clinical problems associated with the treatments and all animals survived to their scheduled end point. The pathologist reported that the ANA device when used in conjunction with the Solitaire™ 2 Revascularization Device had comparable tissue responses to the control FlowGate™ Balloon Guide Catheter device used in conjunction with the Solitaire™ 2 Revascularization Device at 3 days and 30 days.

Example 3: Human Clinical Trial: Prospective, Single-Arm, Multi-Center Study to Assess the Safety and Performance of the ANA Device, in Combination with a Clot-Capture Element (for Example a Stent Retriever (SR)) in Patients with Acute Ischemic Stroke The first patient of the following clinical trial was enrolled last 21$^{th}$ September and it is currently ongoing.

1. Introduction and Objectives

As explained before, the ANA device is a distal access catheter designed to assist in neurovascular procedures by facilitating the insertion and guiding of other devices (i.e. retrieval devices and intravascular catheters) and restricting blood flow at the target position. In this particular example, the ANA device is a sterile, single-use, disposable intravascular device comprised of two coaxial catheters (the delivery catheter 3 and the expandable-tip aspiration catheter 7) consisting of sections of variable stiffness. The expandable-tip aspiration catheter 7 comprises a radiopaque nitinol braid (self-expanding funnel 1), covered by a continuous silicone coating that, when deployed, provides local and temporary flow restriction. The delivery catheter 3 has a hydrophilic coating to reduce friction during use and a radiopaque marker on the distal end. Both catheters 1, 7 have Luer lock hubs on their proximal end.

The proposed study has been designed to collect prospective clinical evidence to compare the ANA device to similar devices used for guiding and supporting stent retrievers during neurothrombectomy procedures. The protocol has been designed to replicate the patient population enrolled in prior studies of similar devices. The primary endpoint is the ability of the ANA device to facilitate stent retriever deployment and neurothrombectomy in the anterior circulation, with successful reperfusion defined as achieving a modified Thrombolysis in Cerebral Infarction (mTICI) score of ≥2b in the target vessel with ≤3 passes of the ANA device without the use of rescue therapy. Follow-up at 24 h, Day 5 (+/−12 h) or discharge, whichever comes first, and at 90 days, allow documentation of the clinical outcome of the neurothrombectomy procedure as a whole and other complications, making use of the ANA device for distal access. The study has been conducted in accordance with the Standard ISO 14155 (Clinical investigation of medical devices for human subjects—Good clinical practice).

The objective of the study is to assess safety and performance of the ANA catheter system to be used as a tool and to facilitate the Solitaire stent retriever placement and to provide temporary restriction of blood flow in stroke patients undergoing neurothrombectomy for an acute large vessel occlusion (LVO), presenting (to the neuroimaging laboratory) within 8 h of symptom onset (last time the subject was seen well).

2. Methods

Primary Endpoints:

The performance has been assessed as the ability of the ANA device to facilitate stent retriever deployment and to perform neurothrombectomy in the anterior circulation, with successful reperfusion defined as achieving a modified Thrombolysis in Cerebral Infarction (mTICI) score of ≥2b in the target vessel with ≤3 passes of the ANA device without the use of rescue therapy.

The safety has been assessed as the occurrence of all serious adverse device effects up to 90 days post-procedure, including symptomatic IntraCerebral Hemorrhage (sICH), at 24 h (−8/+12 h) post-procedure.

Secondary Endpoints:

The secondary performance endpoints for this study are as follows:

- The ability of the ANA device to reach the occlusion in the large vessel allowing navigation and deployment of the stent retriever to attempt neurothrombectomy and, at a minimum, passing the bulb of the internal carotid artery in the anterior cerebral circulation.
- Procedure time, defined as time from puncture to achievement of mTICI≥2b with ≤3 passes or if not obtained, to the final angiogram.
- Time to treat, defined as time from door to puncture to first baseline angiogram and to achievement of mTICI≥2b with ≤3 passes or if not obtained, to the final angiogram.
- Neurological status at Day 5 (+/−12 h) or discharge, whichever comes first, and at 90 days (+/−14 days), determined by NIHSS score.
- Modified Rankin Scale (mRS) score at Day 5 (+/−12 h) or discharge, whichever comes first, and at 90 days.

The secondary safety endpoints for this study are as follows:

- Evaluation of IntraCerebral Hemorrhage (ICH); any symptomatic or asymptomatic ICH at 24 h (−8/+12 h), as assessed by magnetic resonance imaging (MRI)/computed tomography (CT). ICH is defined as any extravascular blood in the brain or within the cranium. The ICH is considered symptomatic if it is associated with clinical deterioration (worsening National Institutes of Health Stroke Scale [NIHSS] score of ≥4 points) or leads to death and is identified as the predominant cause of the neurological deterioration, as adjudicated by an independent clinical event committee.
- Incidence of subjects with a neurological deterioration of ≥4 points on NIHSS at 24 h (−8/+12 h), as assessed by an independent investigator (i.e. not involved in patient screening or the thrombectomy procedure).
- Occurrence of embolization in a previously uninvolved territory on the cerebral angiogram.
- Procedure-related mortality rate at Day 5 (+/−12 h) or discharge, whichever comes first.
- Occurrence of procedural complications: arterial perforation, arterial dissection and vasospasm in the target vessel and embolization in a previously uninvolved vascular territory.
- Occurrence of infarction in a previously uninvolved vascular territory, as assessed from 24-h imaging (MRI/CT) post-procedure.

Study Sites and Population Sample Size:

The study has been conducted at up to five (5) high volume, comprehensive stroke centers (available 24 h/7 days) within the European Union. Currently, the proposed sites are in Spain, but other European countries could be added at a later time. The involved stroke centers are Hospital Germans Trias i Pujol, Hospital de Bellvitge, Hospital Clinic, Hospital Vall d'Hebron, Hospital las Cruces de Bilbao.

The population has been based on patients with Acute Ischemic Stroke (AIS), whose stroke is attributable to an occlusion of a large artery in the neurovasculature, such as the internal carotid artery, M1 or M2 segments of the middle cerebral artery, and who are either ineligible for IV alteplase (tissue-type Plasminogen Activator [t-PA]) or have received IV t-PA therapy without sufficient recanalization, but are within the timeframe of 8 h from symptom onset (last seen well) to groin puncture in the catheterization lab. Hundred and twenty-five (125) consecutive subjects indicated for treatment with an ANA device in combination with the Solitaire stent retriever has been set to be enrolled. Inclusion and exclusion criteria for the selection of the patients are described in detail in the clinical trial protocol.

It is estimated that the study will take approximately 5 to 6 patients/month/center or 25 to 30 patients per month, hence a duration of 5-6 months, to enroll 125 subjects. Each patient will dedicate a duration of participation of 90 days+/−2 weeks. As analysis, when patient 35 is at Day 5 (+/−12 h) or discharge, which includes the primary performance and early secondary endpoints, an interim analysis is performed, and an interim study report prepared.

The following study population has been defined for the purpose of statistical analysis:

- Enrolled population: defined as all subjects who have given their informed consent to participate in the study.
- Intent-To-Treat (ITT): defined as all subjects enrolled in the study who attended the procedure.
- Modified Intent-To-Treat (mITT): defined as all subjects from the ITT analysis set, with the exclusion of roll-in subjects. A roll-in subject is defined by the first subject from each investigator.

Study Procedures and Assessments:

The following Table 10 shows the schedule of assessments recorded during the baseline, during the procedure, and the assessments which should be completed at 24-h post-procedure, at Day 5 (+1-12 h) or discharge (whichever comes first, depending on whatever time point is earliest) and at the 90-day follow-up office visit.

TABLE 10

Schedule of assessments

| Event | Screening/ Baseline | Procedure | 24 h Post-procedure | Day 5 +/− 12 h/ Discharge (whichever is earliest) | Day 90 +/− 14 days |
|---|---|---|---|---|---|
| Eligibility criteria (inclusion/exclusion) | X | | | | |
| Informed consent | X | | | | |
| Demographic/medical history | X | | | | |
| Physical exam (blood pressure, heart rate) | X | | | | |

TABLE 10-continued

| Schedule of assessments | | | | | |
|---|---|---|---|---|---|
| Event | Screening/ Baseline | Procedure | 24 h Post-procedure | Day 5 +/− 12 h/ Discharge (whichever is earliest) | Day 90 +/− 14 days |
| Baseline laboratory assessments | X | | | | |
| Pregnancy test (as applicable) | X | | | | |
| 12-lead electrocardiogram (ECG) | X | | | | |
| Modified Ranking Scale (mRS) | X | | | X | X |
| National Institute of Health Stroke Scale (NIHSS) | X | | X | X | X |
| Neuro imaging (MRI/CT) | X | | X | | |
| Angiogram | | X | | | |
| Mechanical thrombectomy | | X | | | |
| Adverse events | X | X | X | X | X |
| Concomitant medications | X | X | X | X | X |

All thrombectomy patients presenting at the participating study sites after study start has been tracked anonymously on a patient screening log, for any patient not included in the study; the reason for non-inclusion has been documented on the screening log.

Analysis Methodology:

Statistical analyses are done using SAS System®, Version 9.4 or further, and a complete statistical analysis plan is written before the conduct of analysis: a complete description of all derived variables used in the reporting is given, as well as the statistical tables and listings to be generated.

All statistical analyses are made on locked databases following data clarifications resolved due to data management processes.

Primary analysis set for statistical reporting is the ITT population, with no replacement of missing data planned in the statistical analysis to provide unbiased results. However, two sensitivity analyses are conducted in regard to the missing values for the primary performance endpoint. The first one imputes failures instead of missing value, in a conservative approach. The second one uses the repartition of success/failure reported on non-missing value to impute the missing values with the same repartition. In both sensitivity analyses, the same statistical testing is presented. In addition, primary endpoints are reported on the mITT population.

Except for the primary performance endpoint, no statistical testing is conducted for any parameters in the study and only descriptive analysis is provided to fully describe the parameters recorded. Primary performance endpoint is analyzed using a binomial test as indicated in the study protocol (section 15.1). Heterogeneity of results on the primary endpoint is assessed by comparing the percentage of success among sites using a bilateral Chi-Squared test at the 5% level. In addition, the same analysis is provided by pooling sites from the same towns. These analyses are done on the ITT population only.

When subject 35 is at Day 5 (+/−12 h) or discharge, which includes the primary performance and early secondary endpoints, an interim analysis is performed and an interim study report prepared.

Continuous variables are summarized using standard quantitative statistics: number of non-missing observations, mean, standard deviation, median, quartiles and range (minimum and maximum observed values). The number of missing observations is also specified.

Categorical variables are summarized using classical frequency statistics: number of non-missing observations and percentages by categories. Percentages are calculated on the number of non-missing observations. The number of missing observations is also specified.

When applicable, bilateral asymptotic or exact confidence intervals (CIs) for binomial distributions are calculated at the 95% level (unadjusted 95% CI).

Primary endpoints and early secondary endpoints are assessed both on ITT and mITT populations. Other secondary endpoints are assessed on ITT population only.

AE data is summarized using descriptive statistics: total number of events and number of subjects with at least one of the respective categories AEs, ADEs, SAEs, SADEs and device deficiencies. The severity and the causal relationship are presented.

Figure 20:
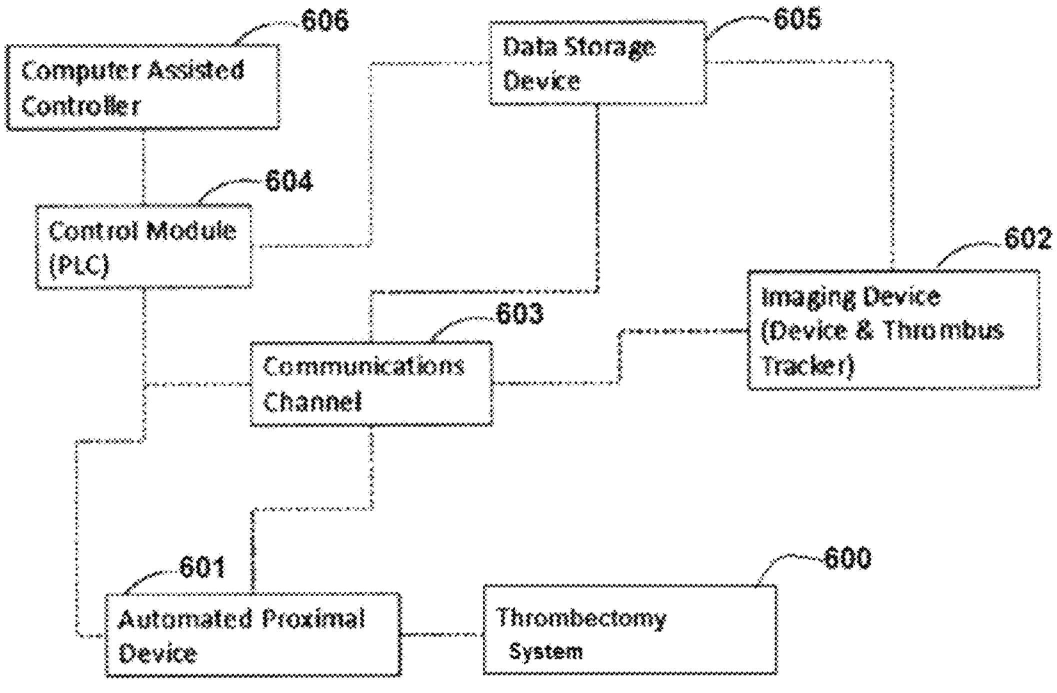
FIG. 20 is a diagram illustrating an automated thrombectomy system (ANCD) according to an embodiment of the present invention.

With reference now to FIG. 20, this figure depicts another example of the proposed thrombectomy system (or ANCD) 600 which allows for its automated maneuvering through a vascular system. According to this particular example, an automated proximal device 601 provides a guidance system to deploy the ANCD 600. Moreover, an imaging device 602 can detect the radiopaque markers included in the segment 10, and also in the delivery catheter 3, and a communications channel 603 can be used to provide means to transport the image to a control module 604. The control module 604 is programmed or configured to allow for guidance of the deployment of the ANCD 600 and storage of data on a data storage device 605. The control module 604 may be a programmable logic controller, a computer, or the like. In this particular embodiment the control module 604 is guided by a computer assisted controller 606. The communications channel 603 can be Ethernet, WiFi, Bluetooth, or the like. The control module 604 is programmed to guide a physician or technician operating the ANCD 600 which allows for the ANCD 600 to be used in non-hospital settings such as nursing homes or assisted care living facilities.

By allowing the ANCD 600 to be used "in the field" the time required to perform the thrombectomy is greatly reduced significantly improving patient outcomes. The control may also be via a controller such as those in use in other current medical devices. In another embodiment, the system may be controlled manually.

Although illustrated and described above with reference to certain specific embodiments, the present invention is however not intended to be limited to the details shown. Rather, various modifications may be made in the details within the scope and range of equivalents of the claims.

The scope of the present invention is defined in the following set of claims.

CITED REFERENCES

Fennell V S, et al. "What to do about fibrin rich 'tough clots'? Comparing the Solitaire stent retriever with a novel geometric clot extractor in an in vitro stroke model", J NeuroIntervent Surg 2018; 0:1-4. doi:10.1136/neurintsurg-2017-013507

Duffy S, Farrell M, McArdle K, Thornton J, Vale D, Rainsford E, Morris L, Liebeskind D S, MacCarthy E, Gilvarry M. Novel methodology to replicate clot analogs with diverse composition in acute ischemic stroke. J Neurointery Surg. 2017 May; 9(5):486-491.

Mokin M, Setlur Nagesh S V, Ionita C N, Mocco J, Siddiqui A H. Stent retriever thrombectomy with the Cover accessory device versus proximal protection with a balloon guide catheter: in vitro stroke model comparison. J Neurointery Surg. 2016 April; 8(4):413-7.

The invention claimed is:

1. A thrombectomy system, comprising:

a delivery catheter configured to be advanced through vasculature of a patient to a thrombus site within a blood vessel;

an aspiration catheter adapted to apply suction to an expandable aspiration funnel extending from a distal end of the aspiration catheter, the aspiration funnel being configured to be movably disposed within the delivery catheter in a retracted position in a compressed state and at least partially outside the delivery catheter in an expanded position, the aspiration funnel having a first tubular section and a second tubular section, the second tubular section proximal to the first tubular section, the second tubular section comprising a first sub-section having a shape with a progressive reduction of diameter configured to open and create a space for the thrombus, and a second sub-section of a tubular uniform diameter extending between aspiration catheter and the first sub-section, wherein each of the first tubular section and the second tubular section is formed by a mesh of at least two helicoidal filaments turning respectively in opposite directions and being intertwined, and extending continuously through the first tubular section and the second tubular section, wherein a braiding angle of the at least two sets of helicoidal filaments within the first tubular section is configured to provide outward radial forces higher than in the second tubular section, wherein the at least two sets of helicoidal filaments form closed loops at a distal end of the first tubular section to act as a spring to further provide the outward radial forces, the aspiration funnel comprising a non-permeable covering, wherein in the expanded position the second tubular section has a diameter smaller than a diameter of the first tubular section, and a diameter of a distal end of the aspiration funnel being greater in the expanded position than in the retracted position, the aspiration funnel being configured to adapt its shape and length to an inner wall of the blood vessel such that in the expanded position a length of the first tubular section from the closed loops to the first sub-section becomes appositioned against the inner wall of the blood vessel to occlude blood flow through the blood vessel, and further wherein the aspiration funnel length increases when it narrows to retain a thrombus within the aspiration funnel;

a clot-capture element comprising closed cells configured to capture the thrombus and to be at least partially withdrawn with the captured thrombus into the aspiration funnel; and a microcatheter adapted to carry the clot-capture element to the thrombus site, wherein the clot-capture element is configured to be movably disposed within the microcatheter in a retracted position, and wherein the microcatheter is configured to be movably disposed within the aspiration catheter.

2. The thrombectomy system according to claim 1, wherein the delivery catheter, the aspiration funnel, the microcatheter and the clot-capture element are oriented on a same axis, are coaxially configured and movable to each other.

3. The thrombectomy system according to claim 1, wherein the aspiration funnel is self-expandable.

4. The thrombectomy system according to claim 1, wherein the clot-capture element is a stent retriever device.

5. The thrombectomy system according to claim 1, wherein the clot capture element has a continuous scaffold.

6. The thrombectomy system according to claim 1, wherein the first sub-section is cone-shaped.

7. The thrombectomy system according to claim 1, wherein the at least two sets of helicoidal filaments are adapted to become more longitudinally aligned as the aspiration funnel lengthens and narrows.

8. The thrombectomy system according to claim 1, wherein the at least two sets of helicoidal filaments are made of a metal, a metal alloy or a composite including Nitinol or Nitinol/Platinum.

9. The thrombectomy system according to claim 8, wherein the helicoidal filaments of the mesh are made of a composite comprising Nitinol/Platinum with a percentage of Platinum from 10% to 40%.

10. The thrombectomy system according to claim 1, wherein: the at least two sets of helicoidal filaments comprise a number ranging between 24 and 48, said filaments having a cross section comprised in a range between 40 and 60 pm; and the angle of the at least two sets of helicoidal filaments with regard to a longitudinal axis of the aspiration funnel is comprised between 50 and 65 degrees for the first section, and between 15 and 50 for the second section.

11. The thrombectomy system according to claim 10, wherein:

the first section comprises a length ranging between 4 and 40 millimeters and the second section comprises a length ranging between 1 and 10 millimeters;

the first section comprises an outer diameter ranging between 3.5 and 6 millimeters and the second section comprises an outer diameter ranging between 1 and 2 millimeters; and the shape of the first sub-section comprises a generatrix with an angle comprised between 15 and 45 degrees with regard to a longitudinal axis of the aspiration funnel.

12. The thrombectomy system according to claim 1, wherein the non-permeable covering comprises a polymer including silicone or polyurethane.

13. A method of extracting a thrombus from a thrombus site in a blood vessel of a patient, the method comprising:

advancing a delivery catheter through vasculature toward the thrombus site;

placing a distal end of the delivery catheter proximal to the thrombus in the blood vessel;

advancing an aspiration catheter within the delivery catheter, an aspiration funnel extending distally from the aspiration catheter, the aspiration funnel comprising a mesh of at least two sets of helicoidal filaments turning respectively in opposite directions and being intertwined, and wherein the at least two sets of helicoidal filaments of the mesh extend continuously through a first tubular section and a second tubular section distinct from and proximal to the a first tubular section wherein a braiding angle of the at least two sets of helicoidal filaments of the first tubular section is configured to provide outward radial forces higher than in the second tubular section, the aspiration funnel further comprising a first sub-section having a shape with a progressive reduction of diameter configured to open and create a space for the thrombus, and a second sub-section of a tubular uniform diameter configured to provide a connection to the aspiration catheter;

moving the aspiration catheter and delivery catheter with respect to each other to place the aspiration funnel outside of the delivery catheter proximal to the thrombus;

expanding the first section and the second section of the aspiration funnel with closed loops formed by the at least two sets of helicoidal filaments at the distal end of the first tubular section, wherein the closed loops act as springs to expand the first tubular section and place a length of the first tubular section from the closed loops to the first sub-section into contact with an inner wall of the blood vessel;

occluding blood flow past the aspiration funnel;

advancing a clot-capture element distally through the aspiration funnel toward the thrombus;

deploying the clot-capture element to capture the clot;

moving the clot-capture element and thrombus proximally toward the aspiration funnel;

applying suction through the aspiration catheter to the aspiration funnel to aspirate the thrombus at least partially into the aspiration funnel; and moving the aspiration funnel and the thrombus proximally within the vasculature, the aspiration funnel adapting its shape and length to a surrounding blood vessel by lengthening as it narrows to retain the thrombus within the aspiration funnel.

14. The method of claim 13, further comprising advancing a microcatheter within the aspiration catheter, the clot-capture element being disposed within the microcatheter.

15. The method of claim 14, further comprising:

moving the microcatheter and clot-capture device with respect to each other to place the clot-capture device outside of the microcatheter; and expanding the clot-capture device.

16. The method of claim 15, wherein expanding the clot-capture device comprises allowing the clot capture device to self-expand.

17. The method of claim 16, wherein advancing the microcatheter comprises advancing a distal end of the microcatheter through the thrombus.

18. The method of claim 13, further comprising moving the clot-capture device proximally at least partially into the aspiration funnel.

19. The method of claim 13, wherein expanding the aspiration funnel comprises allowing the aspiration funnel to self-expand.

20. The method of claim 13, further comprising moving the two sets of helicoidal filaments to a more longitudinally aligned position as the aspiration funnel lengthens and narrows.

21. An automated system configured for automated maneuvering of the thrombectomy system of claim 1 to the blood vessel, the system comprising an automated proximal device configured to provide a guidance system to deploy the thrombectomy system, an imaging device, a communications channel, a control module configured to allow for guidance of the deployment of the thrombectomy apparatus, a data storage device, and a computer assisted controller configured to guide the control module.

* * * * *